(12) United States Patent
Apfel

(10) Patent No.: US 8,871,159 B1
(45) Date of Patent: Oct. 28, 2014

(54) PREPARATION OF CELLS, CELL AGGREGATES AND TISSUE FRAGMENTS

(71) Applicant: Christian Apfel, Larkspur, CA (US)

(72) Inventor: Christian Apfel, Larkspur, CA (US)

(73) Assignee: Christian Apfel, Larkspur, CA (US)

( * ) Notice: Subject to any disclaimer, the term of this patent is extended or adjusted under 35 U.S.C. 154(b) by 0 days.

(21) Appl. No.: 14/109,874

(22) Filed: Dec. 17, 2013

(51) Int. Cl.
*A61B 10/00* (2006.01)
*G01N 1/28* (2006.01)

(52) U.S. Cl.
CPC ................................. *G01N 1/286* (2013.01)
USPC ................ 422/536; 422/63; 422/64; 422/65; 422/67; 436/180

(58) Field of Classification Search
CPC ....... A61B 17/00; A61B 17/32; A61B 17/064
USPC ................ 422/536, 63–67; 436/180
See application file for complete search history.

(56) References Cited

U.S. PATENT DOCUMENTS

| 2010/0136690 A1 | 6/2010 | Sundström et al. |
| 2010/0249785 A1* | 9/2010 | Betts .............................. 606/79 |

* cited by examiner

*Primary Examiner* — Jyoti Nagpaul
(74) *Attorney, Agent, or Firm* — Duane Morris LLP; Siegfried J.W. Ruppert

(57) ABSTRACT

This invention provides compositions and methods useful for the processing of a tissue sample and the preparation of cells, cell aggregates and/or tissue fragments. The invention provides two-stage filer devices and two-membrane devices. Cell aggregates and/or tissue fragments prepared using such devices and according to methods of the present invention can be used in a variety of assay systems, including, but not limited to, drug validation assays, drug screening assays, proliferation assays, metabolic assays, metastasis assays, angiogenesis assays, binding assays, biochemical assays, cellular assays, genetic assays, and the like.

30 Claims, 8 Drawing Sheets

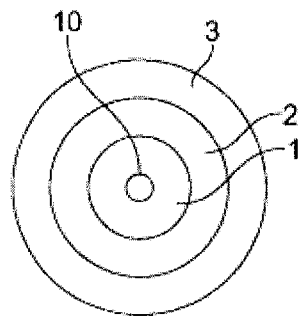
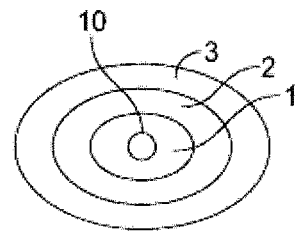
FIG. 2A  FIG. 2B
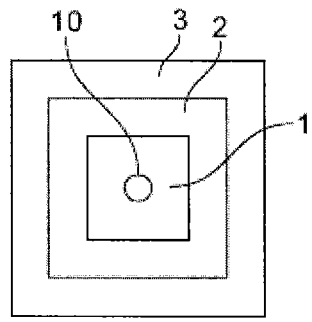
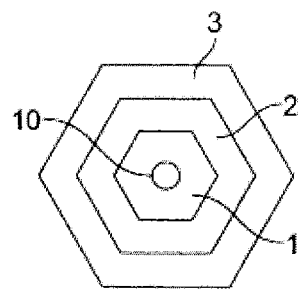
FIG. 2C  FIG. 2D
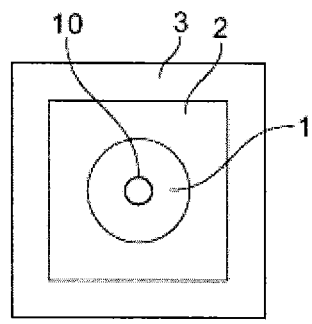
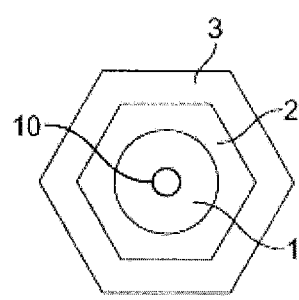
FIG. 2E  FIG. 2F
Figure 2

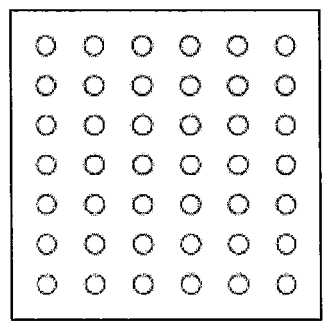
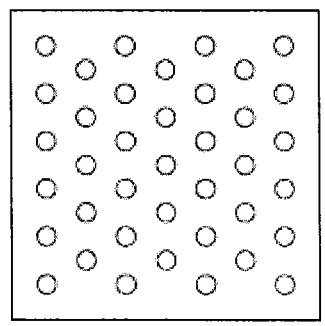
FIG. 5A          FIG. 5B
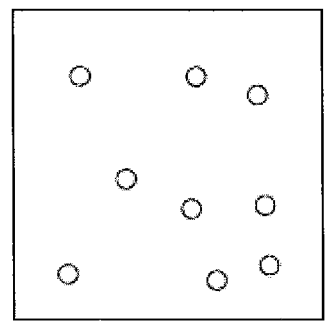
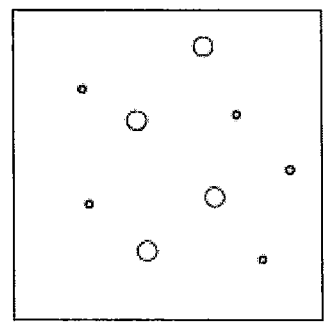
FIG. 5C          FIG. 5D
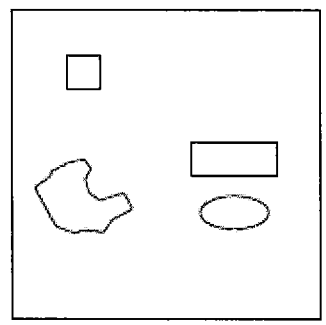
FIG. 5E
Figure 5

US 8,871,159 B1

PREPARATION OF CELLS, CELL AGGREGATES AND TISSUE FRAGMENTS

STATEMENT REGARDING FEDERALLY SPONSORED RESEARCH

This invention was made without Government support.

FIELD OF THE INVENTION

The present invention relates to compositions and methods of processing tissue samples to prepare a plurality of cells, a plurality of cell aggregates and/or tissue fragments.

BACKGROUND OF THE INVENTION

The biology of cells is typically examined in cell monolayer culture applications, however, they have inherent limitations for studying the effects of and screening for drugs and predicting in vivo physiological responses (Girard et al., 2013, *PLoS ONE*, 8(10):e75345). As is known in the art, in vitro single cells or cell monolayer behave very differently from an in vivo organization of cells, wherein the cells are organized in a sophisticated cellular network and form tissues. In those networks, cellular responses of individual cells to drugs may be, at least to a certain extent, controlled by its extracellular environment within such network or tissue. Such extra-cellular environment, for example, includes cell-cell interaction and cell-matrix interactions. Particularly, cell-matrix interactions plays an important role in the formation of tumors and progression of tumors.

Tumor cell aggregates are believed to exhibit specific characteristic traits of their in vivo tumor counterparts. Through their more realistic demonstration of a tumor's in vivo architecture, cell-cell interactions and cell-matrix interactions, they provide more valuable information regarding the cellular differentiation, proliferation, apoptosis and gene expression of the tumor cells in question (Kim et al., 2004, *Breast Cancer Research and Treatment*, 85:281-291). Additionally, the use of tumor cell aggregates or tumor spheroids in drug screening assays allows one to observe the important interactions and behaviors of different cell types, and in particular, stroma cells.

For the reasons discussed above, it is particularly desirable to provide for drug validation and drug screening assays using cell aggregates or tissue fragments, which mimic more the physiological environment from where they are obtained than single cells. As such, there is a long felt need in the art to provide compositions and methods for the preparation of cell aggregates and/or tissue fragments which more accurately reflect the in vivo structure of a tissue, and more specifically, the in vivo structure of a cancerous tissue. Applicant herewith provides compositions and methods useful for the processing of tissues and for the generation of a plurality of cells, a plurality of cell aggregates and/or tissue fragments. Tissues processed according to Applicant's invention can be used in various assay systems, including, but not limited to, drug validation assays, drug screening assays, proliferation assays, metabolic assays, metastasis assays, angiogenesis assays, binding assays, biochemical assays, cellular assays, genetic assays, and the like.

BRIEF SUMMARY OF THE INVENTION

This invention describes devices and methods to process tissue to retrieve tissue fragments and cell aggregates of a desired size to be cultured, transported, and/or examined in assay systems. This is primarily achieved through mechanical dissociation to yield a high proportion of tissue fragments and cell aggregates having desired properties as the tissue from which they were generated. One non-limiting application is the processing of human cancer tissue for drug development and/or for personalizing cancer regimens.

The present invention provides various devices for processing a tissue sample to prepare cell aggregates and/or tissue fragments. In some embodiments of the present invention, such device comprises a first container comprising a first wall, a plurality of cutting blades having a sharp edge pointing inwards into the first container and a first plurality of pores located in the first wall of the first container. The plurality of blades, upon contacting the tissue sample, is capable of processing the tissue sample to prepare a cell aggregate or tissue fragment. The first plurality of pores comprises pore members having a size permitting a single cell and a cell aggregate to pass through, but not permitting the tissue sample to pass through. Typically, a rotational force is used to transport the single cell and the cell aggregate through the first plurality of pores.

Pores of the first plurality of pores may have various sizes. In some embodiments of the present invention, the pores of the first plurality of pores is selected to permit passing through of a single cell and a cell aggregate comprising more than 10 cells but essentially do not permit passing through of a majority of tissue fragments comprising more than about 10,000 cells. In some embodiments, the first plurality of pores comprises pores ranging in size from about 50 µm to about 100 µm, from about 100 µm to about 200 µm, from about 200 µm to about 300 µm, from about 300 µm to about 400 µm, from about 400 µm to about 500 µm, from about 500 µm to about 600 µm or. from about 600 µm to about 1,000 µm.

The shape of the first container can vary. In some embodiments of the present invention, the shape of the first container is selected from the group consisting of cylindrical, oval, rectangular, square, and hexagonal.

The plurality of cutting blades can be attached to various means. In some embodiments of the present invention, the plurality of cutting blades is attached to a shaft. Upon activation of the device, the shaft and the plurality of cutting blades rotate inside the first container.

The plurality of blades can rotate at various rotational speeds. In some embodiments of the present invention, the plurality of cutting blades rotate at a speed selected from the group of ranges consisting of from about 50 rpm to about 200 rpm, from about 100 rpm to about 500 rpm, from about 200 rpm to about 1,000 rpm, from about 500 rpm to about 2,000 rpm, from about 2,000 rpm to about 3,000 rpm, from about 3,000 rpm to about 5,000 rpm, and from about 5,000 rpm to about 10,000 rpm.

In some embodiments of the present invention, the device further comprises an inlet for introducing a cell culture medium.

In some embodiments of the present invention a device further comprises a second container and wherein the first container is nested within the second container. The second container comprises a second wall. In some embodiments of the present invention, the second wall comprises a second plurality of pores. Typically, the size of the pores of the second plurality of pores is different than the size of the pores of the first plurality of pores. In some embodiments of the present invention, the pores of the first plurality of pores are larger in diameter than the pores of the second plurality of pores.

In some embodiments of the present invention, the pores of the second plurality of pores is selected to permit passing through of a single cell but such that they essentially do not permit passing through of a majority of cell aggregates comprising more than 10 cells.

Pores of the second plurality of pores may have various sizes. In some embodiments of the present invention, pores of the second plurality of pores have a diameter ranging from about 10 μm to about 50 μm.

The shape of the second container can vary. In some embodiments of the present invention, the shape of the second container is selected from the group consisting of cylindrical, oval, rectangular, square, and hexagonal.

In some embodiments of the present invention, the second container comprises a collection channel for collecting the cell aggregate. In some embodiments of the present invention, the second container further comprises a gate at the collection channel.

In some embodiments of the present invention a device further comprises a third container and wherein the second container is nested within the third container. The third container comprises a third wall.

The shape of the third container can vary. In some embodiments of the present invention, the shape of the third container is selected from the group consisting of cylindrical, oval, rectangular, square, and hexagonal.

In some embodiments of the present invention, the third container comprises a channel permitting transporting a cell culture medium from the third container into the first container.

In some embodiments of the present invention, the third container comprises a channel permitting collection of cells.

The present invention also provides methods of using a device described herein for processing a tissue sample to prepare a cell aggregate and/or tissue fragment. In some embodiments of the present invention, a method for processing a tissue sample to prepare a cell aggregate and/or tissue fragment using a device described herein, comprises the steps of placing a tissue sample into a device, contacting the tissue sample to the plurality of blades of the device, applying a rotational force, and permitting passing of a cell aggregate through the first plurality of pores of the device. Thereby the tissue is processed to generate a cell aggregate and/or a tissue fragment.

A tissue sample may be obtained in various ways. In some embodiments of the present invention, the tissue sample is obtained by a needle biopsy obtained from a subject. In some embodiments of the present invention, the tissue sample is obtained by a surgical biopsy obtained from a subject.

Various tissue samples can be processed using a device and method of the present invention. In some embodiments of the present invention, the tissue sample is a cancerous tissue sample.

Various cancer tissue samples can be processed using a device and method of the present invention. In some embodiments of the present invention, a cancer tissue sample is selected from the group consisting of a lung cancer tissue, a sarcoma tissue, a gastrointestinal cancer tissue, a genitourinary tract cancer tissue, a liver cancer tissue, a skin cancer tissue, a gynecological cancer tissue, a bone cancer tissue, a nervous system cancer tissue, a hematologic cancer tissue, and an adrenal gland cancer tissue.

In some embodiments of the present invention, the cancerous tissue sample comprises a cancer stem cell. Thus, cancer stem cells can be prepared using a device and method of the present invention.

In some embodiments of the present invention, the tissue sample is a disease tissue sample. Various disease tissue samples can be processed using a device and method of the present invention. In some embodiments of the present invention, a disease tissue sample is selected from the group consisting of a cardiovascular disease tissue, an immune- or inflammation related disease tissue, an infectious disease tissue, and a neurologic disease tissue.

Cell aggregates and tissue fragments of various sizes can be prepared using a device and method of the present invention. In some embodiments of the present invention, a cell aggregate prepared comprises from about 10 to about 500 cells. In some embodiments of the present invention, a cell aggregate prepared comprises from about 20 to about 200 cells. In some embodiments of the present invention, a cell aggregate prepared comprises from about 50 to about 100 cells.

Various rotational forces can be applied in a subject method to process a tissue sample and to generate cell aggregates and tissue fragments and to move cells and cell aggregates through a plurality of pores. In some embodiments of the present invention, a rotational force is selected from the group of ranges consisting of from about 50 rpm to about 200 rpm, from about 100 rpm to about 500 rpm, from about 200 rpm to about 1,000 rpm, from about 500 rpm to about 2,000 rpm, from about 2,000 rpm to about 3,000 rpm, from about 3,000 rpm to about 5,000 rpm, and from about 5,000 rpm to about 10,000 rpm.

BRIEF DESCRIPTION OF THE DRAWINGS

FIGS. 2A-F schematically depict top views of various arrangements of a first container 1 nested in a second container 2 and a second container 2 nested in a third container 3. FIG. 2A schematically depicts an all cylindrical arrangement. FIG. 2B schematically depicts an all oval arrangement. FIG. 2C schematically depicts an all rectangular arrangement. FIG. 2D schematically depicts an all hexagonal arrangement. FIG. 2E schematically depicts a cylindrical first container 1 and rectangular second and third containers 2, 3. FIG. 2F schematically depicts a cylindrical first container 1 and hexagonal second and third containers 2, 3. Rotating shaft 10 is optional.

FIGS. 5A-D schematically depict various arrangements of pores within a wall of a container. FIG. 5A schematically depicts a regular arrangement of pores wherein the pores are aligned vertically and horizontally. FIG. 5B schematically depicts a regular arrangement of pores wherein the pores are aligned vertically and offset horizontally. FIG. 5C schematically depicts an irregular or random arrangement of same size pores. FIG. 5D schematically depicts an irregular or random arrangement of different size pores. FIG. 5E schematically depicts pores of different shapes that could be quadratic, rectangular, oval or have any other shape in a random arrangement FIG. 6 schematically depicts an embodiment of a device of the present invention for the processing of a tissue sample to prepare a plurality of cells, a plurality of cell aggregates and tissue fragments. This device embodiment is similar to the device depicted in FIG. 1, however, in this embodiment, channel 12 does not redirect fluid back into first container 1. Rather, fluid and single cells exit the device by passing through gate 14 and, as indicated by the arrow pointing into container 1, new medium or fluid is added freshly into container 1. Containers 1, 2, and 3 may be open or closed at the top (as indicated by a solid line). Individual parts are described in FIG. 1 and herein.

DETAILED DESCRIPTION OF THE INVENTION

I. Definitions

Figure 1:
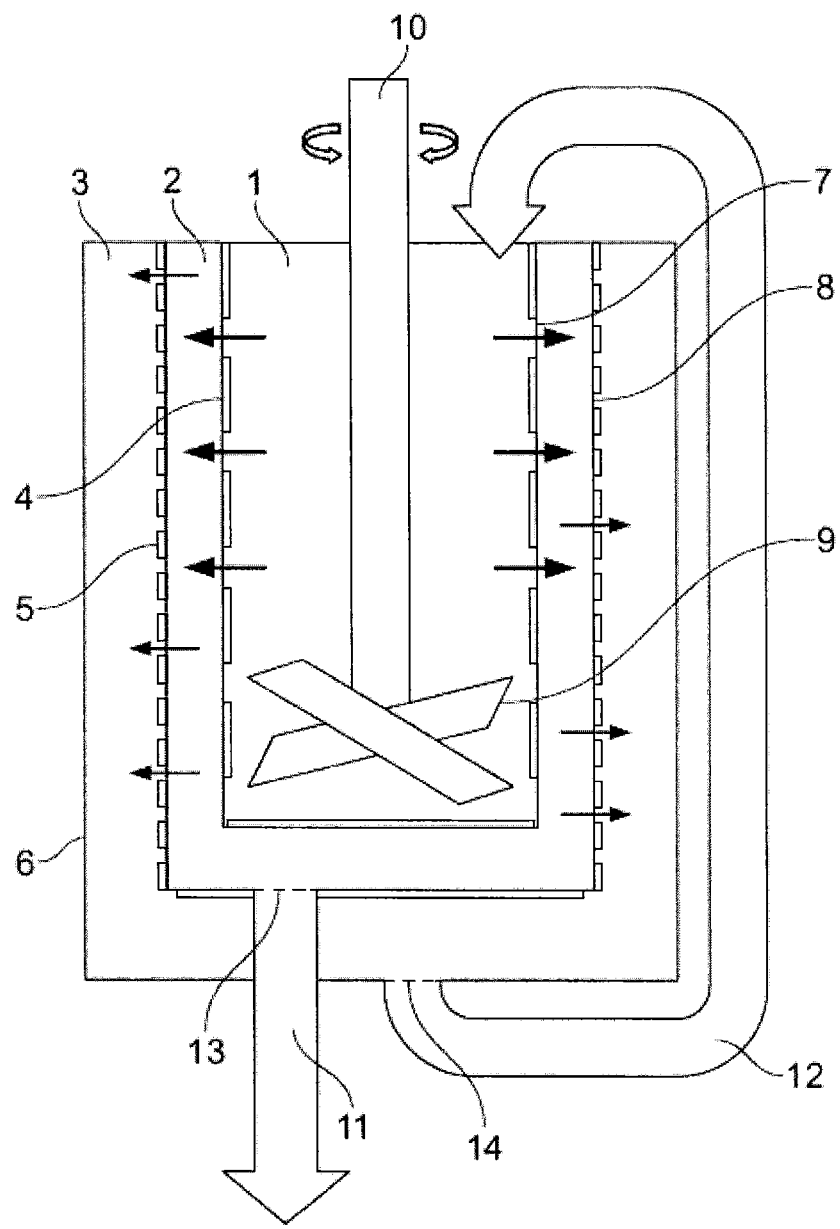
FIG. 1 schematically depicts an embodiment of a device of the present invention for the processing of a tissue sample to prepare a plurality of cells, a plurality of cell aggregates and tissue fragments. The cross-sectional view of a two-stage filter device shows a first container 1 nested in a second container 2 nested in a third container 3. The first container 1 has a first wall 4, the second container has a second wall 5, and the third container 3 has a third wall 6. The first wall 4 comprises a first plurality of pores 7 and the second wall 5 comprises a second plurality of pores 8. The size of pores of a first plurality of pores 7 is different from the size of pores of the second plurality of pores 8. Blade 9 (plurality of blades; two blades are shown), rotating shaft 10, collection channel 11, channel 12. The collection channel 11 and channel 12 optionally have gates 13 and 14, respectively. As schematically depicted in this embodiment, channel 12 re-directs fluid into the first container to, e.g., create a cycling flow of medium and/or cell particles. Arrows pointing through the pores indicate direction of single cells and cell aggregates passing through the pores 7 (thick arrows) and preferably single cells only passing through pores 8 (thin arrows). Containers 1, 2, and 3 may be open or closed at the top (as indicated by a solid line).

Throughout the present specification and the accompanying claims the words "comprise" and "include" and variations thereof such as "comprises," "comprising," "includes," and "including" are to be interpreted inclusively. That is, these words are intended to convey the possible inclusion of other elements or integers not specifically recited, where the context allows. No language in the specification should be construed as indicating any non-claimed element essential to the practice of the invention. As used herein, the term "consisting of" is intended to mean including and limited to whatever follows the phrase "consisting of". Thus the phrase "consisting of" indicates that the listed elements are required or mandatory and that no other elements may be present. The term "consisting essentially of" means that the composition, method or structure may include additional ingredients, steps and/or parts, but only if the additional ingredients, steps and/or parts do not materially alter the basic and novel characteristics of the claimed composition, method or structure.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed the "less than or equal to 10" as well as "greater than or equal to 10" is also disclosed.

All methods described herein can be performed in any suitable order unless otherwise indicated herein or otherwise clearly contradicted by context. Further, all methods described herein and having more than one step can be performed by more than one person or entity. Thus, a person or an entity can perform step (a) of a method, another person or another entity can perform step (b) of the method, and a yet another person or a yet another entity can perform step (c) of the method, etc. The use of any and all examples, or exemplary language (e.g. "such as") provided herein is intended merely to better illuminate the invention and does not pose a limitation on the scope of the invention otherwise claimed.

Units, prefixes, and symbols are denoted in their Système International de Unites (SI) accepted form. Unless otherwise indicated, nucleic acids are written left to right in 5' to 3' orientation; amino acid sequences are written left to right in amino to carboxy orientation.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); The Cambridge Dictionary of Science and Technology (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "about" refers to a range of values of plus or minus 10% of a specified value. For example, the phrase "about 200" includes plus or minus 10% of 200, or from 180 to 220, unless clearly contradicted by context.

As used herein, the term "administering" means the actual physical introduction of a composition into or onto (as appropriate) a host or cell. Any and all methods of introducing the composition into or onto the host or cell are contemplated according to the invention; the method is not dependent on any particular means of introduction and is not to be so construed. Means of introduction are well-known to those skilled in the art, and also are exemplified herein.

As used herein, the terms "agent" or "compound," used interchangeably herein, mean any chemical compound, for example, a macromolecule or a small molecule disclosed herein. The agent can have a formula weight of than about 200,000 grams per mole, less than 150,000 grams per mole, less than 100,000 grams per mole, less than 75,000 grams per mole, less than 50,000 grams per mole, less than 25,000 grams per mole, less than about 10,000 grams per mole, less than 5,000 grams per mole, less than 1,000 grams per mole, or less than about 500 grams per mole. The agent can be naturally occurring (e.g., a herb or a nature product), synthetic, or both. Examples of macromolecules are proteins, protein complexes, and glycoproteins, nucleic acids, e.g., DNA, RNA and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds. An agent can be the only substance used by the method described herein. Alternatively, a collection of agents can be used either consecutively or concurrently by the methods described herein. Alternatively, an agent can be a small molecule attached covalently or non-covalently to a macromolecule.

As used herein, the term "animal" refers to a multicellular organism of the kingdom Animalia, more preferably, to a mammal, more preferably to a primate and most preferably, to a human.

As used herein, the term "animal model" refers to a non-human animal that faithfully mimics a human disease and in which potential therapeutic compositions or potentially harmful compositions may be evaluated for their effect on the disease.

As used herein, the terms "attach to" or "attached to" or grammatical equivalents thereof mean to fasten on, fasten together, affix to, mount to, mount on, connect to or to join. "Attachment" means the act of attaching or the condition of being attached. Attachment can be direct or indirectly. For example a part A may be attached directly to part B. Alternatively, part A may be attached indirectly to part B through first attaching part A to part C and then attaching part C to part B. More than one intermediary part can be used to attach part A to part B. Attaching can be permanent, temporarily, or for a prolonged time. For example, a cutting blade of the present invention may be attached to a container temporarily for the time necessary to perform a method of the invention or a step of a method of the invention. Alternatively, a cutting blade of the present invention may be attached to a container or to an object or structure for a prolonged time, e.g., also when a method of the present invention or a step of the method of the present invention is not performed. Also, a cutting blade of the present invention may be attached permanently to a container or to an object or structure.

With respect to cells as used herein, the terms "attachment," "attach," "attaches" or grammatical equivalents thereof refer to cells that adhere directly or indirectly to a substrate and to cells that adhere to other cells.

As used herein, the term "biologically active" when referring to an agent or compound is art-recognized and refers to a form of the agent or compound that allows for it, or a portion of the amount of the agent or compound administered, to be absorbed by, incorporated into, or otherwise be physiologically available to a cell, a subject or patient to which/whom it is administered.

As used herein, the term "biological fluid" refers to a fluid from a host and includes whole blood, serum, plasma, urine, tears, mucus ascites fluid, oral fluid, semen, stool, sputum, cerebrospinal fluid and fetal fluid. A biological fluid may include cells or be devoid of cells.

As used herein, the term "biological sample" means a sample of biological tissue or fluid that contains nucleic acids or polypeptides. Such samples are typically from humans, but include tissues isolated from non-human primates, or rodents, e.g., mice, and rats. Biological samples may also include sections of tissues such as surgical biopsy, fine needle aspiration biopsy and autopsy samples, frozen sections taken for histological purposes, blood, plasma, serum, sputum, stool, tears, mucus, hair, skin, etc. Biological samples also include explants and primary and/or transformed cell cultures derived from patient tissues. A "biological sample" also refers to a cell or population of cells or a quantity of tissue or fluid from an animal. Most often, the biological sample has been removed from an animal, but the term "biological sample" can also refer to cells or tissue analyzed in vivo, i.e., without removal from the animal. Typically, a "biological sample" will contain cells from the animal, but the term can also refer to non-cellular biological material, such as non-cellular fractions of blood, saliva, or urine, that can be used to measure expression level of a polynucleotide or polypeptide. Numerous types of biological samples can be used in the present invention, including, but not limited to, a tissue biopsy or a blood sample. As used herein, a "tissue biopsy" refers to an amount of tissue removed from an animal, preferably a mammal, more preferable a primate, and most preferably a human. A "biological sample" encompasses samples that have been manipulated in any way after their procurement, such as by treatment with reagents; washed; or enrichment for certain cell populations, such as CD4+ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like. As used herein, "providing a biological sample" means to obtain a biological sample for use in methods described in this invention. Most often, this will be done by removing a sample of cells from a subject, but can also be accomplished by using previously isolated cells (e.g., isolated by another person, at another time, and/or for another purpose), or by performing the methods of the invention in vivo. Archival tissues, having treatment or outcome history, will be particularly useful. A biological sample can also be derived from an animal which harbors a xenograft tumor implanted from a patient, another animal or a cancer cell line.

As used herein, if, for example, a biological sample is obtained from a patient having a disease, the terms "control" or "control sample," refer to biological sample from a healthy patient or a biological sample from a patient not having the disease.

As used herein, the term "cancerous cell" refers to a cell that exhibits deregulated growth and, in most cases, has lost at least one of its differentiated properties, such as, but not limited to, characteristic morphology, non-migratory behavior, cell-cell interaction and cell-signaling behavior, protein expression and secretion pattern, etc.

As used herein, the term "cancer stem cell" refers to self-renewing and pluripotent cancer cells typically found inside of tumors that may give rise to different types of cells (see, e.g., U.S. Pat. No. 6,984,522). Cancer stem cells can be obtained from any tumor source including primary or any metastatic tumor site, lymph nodes, ascites fluids, or blood. Cancer stem cells are identified by virtue of their functional characteristics that include, without limitation, the ability to repopulate new tumors in serial transplants, and ability to give rise to the functional and phenotypic cellular heterogeneity of the original tumor.

As used herein, the term "carrier" in the context of "pharmaceutically acceptable carrier" refers to an inert substance used as a diluent, adjuvant, excipient or vehicle with which a drug, medicament or vaccine is administered.

As used herein, the terms "cell aggregate," "cell sphere" or "cell spheroid" refer to a plurality of cells that attach to each other through cell-to-cell adhesion or using scaffolds, extracellular matrix components, magnetic nanoparticles with magnets, other nanomaterials and the like as known in the art. As used herein, the term "cell aggregate" can comprise a plurality of cells of a single cell type, a plurality of cells of one cell type combined with a plurality of cells of a different cell type, or a plurality of cells of one cell type combined with multiple pluralities of cells of multiple different cell types.

As used herein, the term "contacting" refers to an instance of exposure of at least one substance to another substance. For example, contacting can include contacting a substance, such as a cell or a biological sample to an agent or compound described herein. A cell can be contacted with the agent, for example, by adding the agent to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of contact with a cell or group of cells is determined by the time the agent is present at physiologically effective (biologically active) levels or at presumed physiologically effective (biologically active) levels in the medium or extracellular fluid bathing the cell. The term "contacting" is used herein interchangeably with the following: combined with, added to, mixed with, passed over, incubated with, flowed over, place in direct physical association with another substance, etc., unless clearly contradicted by context. For example, in some embodiment of the present invention, a tissue sample is contacted with a cell culture medium. In some embodiment of the present invention, a tissue sample is contacted with a blade.

By "determining a functional effect" is meant assaying for a compound that increases or decreases a parameter that is indirectly or directly under the influence of a compound or agent, e.g., physiological, functional, enzymatic, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for a protein of interest, measuring inducible markers or transcriptional activation of a protein of interest; measuring binding activity, e.g., binding to a receptor of interest, measuring cellular proliferation, measuring apoptosis, or the like. Determination of the functional effect of a compound on a cell or on a cell aggregate can be performed using assays known to those of skill in the art such as an in vitro assays, e.g., cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo; mRNA and protein expression in cells undergoing metastasis, and other characteristics of cancer cells. The functional effects can be evaluated by many means known to those skilled in the art, e.g., microscopy for quantitative or qualitative measures of alterations in morphological features, measurement of changes in RNA or protein levels, measurement of RNA stability, identification of downstream or reporter gene expression (CAT, luciferase, β-gal, GFP and the like), e.g., via chemiluminescence, fluorescence, colorimetric reactions, antibody binding, inducible markers, and ligand binding assays. "Functional effects" include in vitro, in vivo, and ex vivo activities. A physiological effect includes, but is not limited to, e.g., killing cells, killing a tissue, causing a cell to die by apoptosis or other mechanism, causing a tissue to die by apoptosis or other mechanism, causing a cell to stop proliferating, causing a tissue to stop proliferating, causing a cell to lose viability, and causing a tissue to lose viability.

As used herein, the term "different" means not the same, not of the same identity.

As used herein, the terms "disorder", "disease" or "pathological condition" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information. Disease specifically includes any kind of cancer and pathological conditions associated with or developing in a subject as a consequence of having cancer.

As used herein, the term "embryonic stem cell" refers to the pluripotent stem cells of the inner cell mass of the embryonic blastocyst (see, e.g., U.S. Pat. Nos. 5,843,780, 6,200, 806). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Illustrative distinguishing embryonic stem cell characteristics include, without limitation, gene expression profile, proliferative capacity, differentiation capacity, normal karyotype, responsiveness to particular culture conditions, and the like.

As used herein, the term "ex vivo" means outside the body of the organism from which a cell or cells is obtained or from which a cell line is isolated.

As used herein, the terms "individual," "host," "subject," and "patient," used interchangeably herein, refer to a mammal, including, but not limited to, murines, felines, simians, humans, mammalian farm animals, mammalian sport animals, and mammalian pets. The term includes mammals that are susceptible to diseases, in particular cancer. A preferred subject is a human.

As used herein, the terms "individual," "host," "subject," or "patient" to be treated for a condition or disease by a subject method means either a human or non-human animal in need of treatment for a condition or disease. A preferred condition is cancer or a condition affected by or caused by cancer.

As used herein, the term "in vitro" means outside the body of the organism from which a cell or cells is obtained or from which a cell line is isolated.

As used herein, the term "in vivo" means within the body of the organism from which a cell or cells is obtained or from which a cell line is isolated.

As used herein, the term "malignant cell" refers to a cell having the property of locally invasive and destructive growth and metastasis. Examples of "malignant cells" include, but not limited to, leukemia cells, lymphoma cells, cancer cells of solid tumors, metastatic solid tumor cells (such as but not limited to breast cancer cells, ovarian cancer cells, prostate cancer cells, lung cancer cells, colon cancer cells) in various body fluids including blood, bone marrow, ascitic fluids, stool, urine, bronchial washes, etc.

As used herein, "mammal" or "mammalian" means or relates to the class mammalia including, but not limited to the orders carnivore (e.g., dogs and cats), rodentia (e.g., mice, guinea pigs, and rats), and primates (e.g., humans, chimpanzees, and monkeys).

As used herein, the term "mammalian cell" includes reference to a cell derived from a mammal including, but not limited to, human, rat, mouse, guinea pig, chimpanzee, or macaque. The cell may be cultured in vivo or in vitro.

As used herein, the terms "metastases" or "metastatic tumor cell" refer to a metastasis from a primary tumor wherein the primary tumor is a solid, non-lymphoid tumor.

As used herein, the term "neoplastic cell" refers to abnormal cells that have uncontrolled cellular proliferation and can continue to grow after the stimuli that induced the new growth has been withdrawn. Neoplastic cells tend to show partial or complete lack of structural organization and functional coordination with the normal tissue, and may be benign or malignant.

The terms "optional" or "optionally" as used throughout the specification means that the subsequently described event or circumstance may but need not occur, and that the description includes instances where the event or circumstance occurs and instances in which it does not. The terms also refer to a subsequently described composition that may but need not be present, and that the description includes instances where the composition is present and instances in which the composition is nor present.

As used herein, the term "plurality" means more than one. For example, a plurality of pores means at least two pores, at least three pores, at least four pores, and the like. Likewise, a plurality of blades means at least two blades, at least three blades, at least four blades, and the like.

As used herein, the terms "polypeptide" and "protein" (used interchangeably herein) refer to a polymer of amino acid residues.

As used herein, the term "population of cells" refers to cells, preferably mammalian cells, more preferably human cells, grown in vitro or in vivo. The term also refers to cells within a host and may comprise a mixture of cells, such as virally infected cells and uninfected cells. Preferred population of cells, without limitation, include, a population of cancer cells, a population of cancer cells within a host, a population of cancer cells comprising a cancer stem cell, a population of cancer cells within a host comprising a cancer stem cell.

As used herein, the term "precancerous cell" refers to a cell characterized by uncontrolled, abnormal growth or a cell derived from such a cell. The term "precancerous cell" includes, for example, a primary precancerous cell obtained from a patient with precancerous disorder or cell line derived from such a cell or a cancer stem cell. Similarly, a "hematological precancerous cell" refers to a precancerous cell deriving from a blood cell or bone marrow cell.

As used herein, the term "precancerous disorder" refers to one of a group of hyperproliferative disorders that can develop into cancer, including, but not limited to, a precancerous blood disorder, such as myeloproliferative disease or myelodysplastic syndrome which is a premalignant condition that is related to and/or can develop into acute myeloid leukemia (AML).

As used herein, the terms "process a tissue sample," "processing a tissue sample" and grammatical equivalents thereof refer to slicing, cutting, cleaving a tissue sample into at least two tissue fragments. A tissue sample can be a complete tissue (e.g., obtainable from a deceased subject) or any part of a complete tissue (e.g., obtainable from a living subject).

As used herein, the term "progenitor cell" refers to a committed, but undifferentiated, cell that can give rise, through one or more cell division cycles, to at least one differentiated cell type. Typically, a stem cell gives rise to a progenitor cell through one or more cell divisions in response to a particular stimulus or set of stimuli, and a progenitor gives rise to one or more differentiated cell types in response to a particular stimulus or set of stimuli.

As used herein, the term "scaffold" or "matrix" refers to any attachment of cells.

As used herein, the term "stem cell" refers to an undifferentiated cell that can give rise, through one or more cell division cycles, to at least one differentiated cell type.

As used herein, the term "substantially not changing," "substantially the same," "substantially uniform," and grammatical equivalents thereof refer to a level, amount, concentration of a parameter, such as a chemical compound, a metabolite, a nucleic acid, a polypeptide, or a physical parameter (such as absorption, half-life, pH, temperature, viscosity, length, width, height circumference, form, shape, weight, angle, etc.) that has an increase or decrease of less than 30%, preferably less than 25%, more preferable less than 20%, even more preferable less than 15% and still more preferably an increase or decrease of less than 10% and most preferably an increase or decrease of less than 5% when compared to the level, amount, concentration of the same parameter or physical parameter of a sample, composition of matter, or object to which it is compared.

As used herein, the term "tissue biopsy" refers to an amount of tissue sample removed from a subject, primarily for the purpose of preparing cells therefrom or for diagnostic purposes. In a patient with cancer, tissue may be removed from a tumor, allowing the analysis of cells within the tumor. "Tissue biopsy" includes any type of biopsy, such as needle biopsy, fine needle biopsy, surgical biopsy, etc.

As used herein, the term "tissue fragment" refers to a part of a tissue sample that is obtained by processing a tissue sample, including but not limited to, slicing, cutting, and cleaving the tissue sample. As used herein, the term "tissue fragment" can comprise a plurality of cells of a single cell type, a plurality of cells of one cell type combined with a plurality of cells of a different cell type, or a plurality of cells of one cell type combined with multiple pluralities of cells of multiple different cell types. A tissue fragment comprises more than 10,000 cells.

As used herein, the term "wall of a container" includes each wall of a container, such as the bottom of the container, the top of the container, and each side of a container. For example, a wall of a cylindrical container includes the bottom, top and the cylindrical wall of the container. Likewise, walls of a hexagonal container include the bottom, the top and each of the six sides of the hexagonal container. Bottom and top walls may be referred to as horizontal walls and side walls as vertical walls, respectively.

Described herein are compositions and methods for the preparation of cells, specifically for cell aggregates and tissue fragments, more specifically for cell aggregates and tissue fragments from a disease tissue. Applicant's approach presents easy, rapid, and cost-effective methods for preparing cells, cell aggregates and tissue fragments.

II. Compounds and Compositions

It is an objective of the present invention to provide novel compositions, devices and methods for processing a tissue sample to prepare a plurality of cells, a plurality of cell aggregates and tissue fragments. More specifically, it is an objective of the present invention to provide compositions and devices that allow the preparation of tissue fragments, cell aggregates and single cells from a tissue sample. The novel devices described herein can be used for the preparation of tissue fragments, cell aggregates and single cells from a tissue sample. Tissue fragments, cell aggregates and single cells prepared according to a subject method can be used in a wide variety of methods, including drug screening assays and drug validity assays for drug development and/or personalizing therapy.

A. Device for Processing a Tissue Sample to Prepare a Plurality of Cells, a Plurality of Cell Aggregates and Tissue Fragments In one aspect, the present invention provides devices for processing a tissue sample to prepare a plurality of cells, a plurality of cell aggregates and tissue fragments. The devices for processing a tissue to prepare a plurality of cells, a plurality of cell aggregates and tissue fragments include devices referred to herein as (1) a two-stage filter device and (2) a two-membrane device, each of which is more fully described below and herein. While each device is suitable to processing a tissue sample to prepare a plurality of cells, a plurality of cell aggregates and tissue fragments, depending on its use and configuration (as further detailed herein and as apparent to one of ordinary skill in the art), the devices may process a tissue sample to predominantly prepare a plurality of cell aggregates, i.e., when looking into the volume of a tissue sample, after processing, the volume of the plurality of cell aggregates combined will be larger than the volume of the plurality of cells combined or the tissue fragments combined.

1. Two-Stage Filter Device

In some embodiments of the present invention a device for processing a tissue sample to prepare a plurality of cells, a plurality of cell aggregates or tissue fragments is a two-stage filter device. A two stage filter device makes use of the different size of single cells, cell aggregates and tissue fragments and can be used to simultaneously prepare tissue fragments, cell aggregates and single cells. Single cells are efficiently separated from the larger cell aggregates and tissue fragments by allowing the single cells to pass through a permeable arrangement through which the larger cell aggregates and tissue fragments cannot pass through. The present invention provides a two-stage filter device for preparing cells. In some embodiments of the present invention the device for preparing cells comprises one or more of the following: a first container, a second container, a third container, and a blade. An exemplary embodiment of a two-stage filter device for preparing cells is shown schematically in FIG. 1.

i. First Container

In some embodiments of the present invention a device for processing a tissue sample to prepare a plurality of cells, a plurality of cell aggregates or tissue fragments comprises a first container. A first container is shown schematically as 1 in the Figures herein. A first container within a two-stage filter device is shown schematically as 1 in FIGS. 1-8 herein.

The shape and size of the first container can vary according to the use and volume of sample being processed as described herein. A certain shape and size of the first container may be chosen by one of ordinary skill in the art depending, e.g., on the size of tissue sample to be processed and other parameters in view of the description herein. In some embodiments, the first container is a cylindrical container. An exemplary arrangement of a cylindrical first container in a two-stage filter is shown schematically in FIGS. 2A, 2E, and 2F. In some embodiments, the first container is an oval container. An exemplary arrangement of an oval first container in a two-stage filter device is shown schematically in FIG. 2B. In some embodiments, the first container is a rectangular container. An exemplary arrangement of a rectangular first container in a two-stage filter device is shown schematically in FIG. 2C. In some embodiments, the first container is a container having four, five, six or more sides. An exemplary arrangement of a hexagonal first container in a two-stage filter device is shown schematically in FIG. 2D.

In some embodiments, a first container comprises substantially vertical walls. For using a two-stage filter device in a method described herein or other methods, the diameter of the first container is not critical. A certain diameter of the first container may be chosen by one of ordinary skill in the art depending, e.g., on the size of tissue sample to be processed and other parameters in view of the description herein. In some embodiments, wherein the first container comprises vertical walls, the first container has a diameter ranging from about 5 mm to about 150 mm, preferably from about 10 mm to about 100 mm, more preferably from about 15 mm to about 50 mm and most preferably from about 20 mm to about 30 mm.

Figure 3:
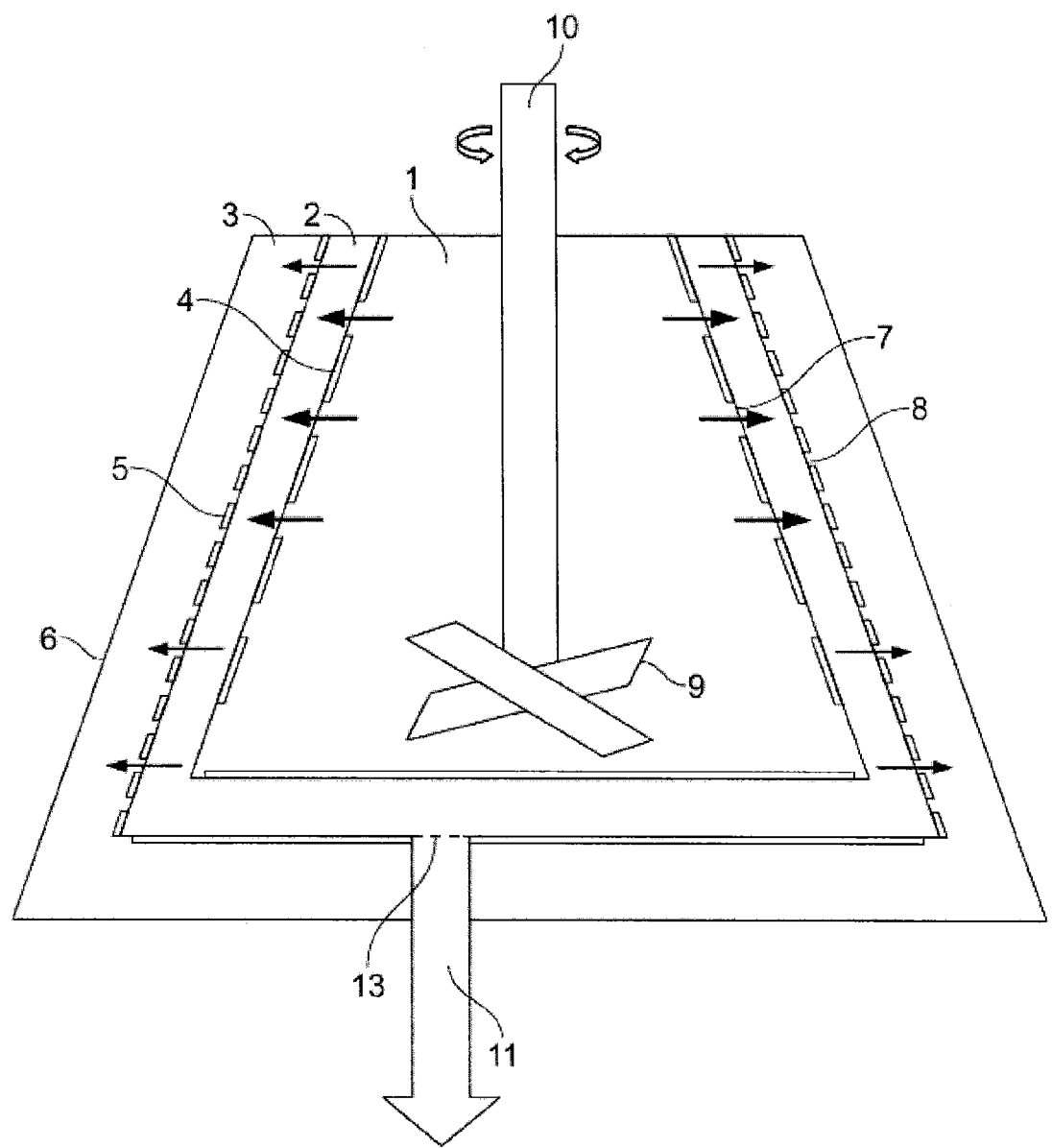
FIG. 3 schematically depicts a two-stage filter device of the present invention wherein the first 1, second 2 and third 3 containers have an upper part that is narrower than the lower part of the first, second, and third containers. Containers 1, 2, and 3 may be open or closed at the top (as indicated by a solid line). The description of parts is as in FIG. 1 and as described herein.

In some embodiments, a first container comprises one or more non-vertical walls. A non-vertical wall, e.g., is a wall arranged at an angle. In some embodiments, the upper part of the first container is narrower than the lower part of the first container. An exemplary embodiment of a two-stage filter wherein the upper part of the first container is narrower than the lower part of the first container is schematically shown in FIG. 3.

For using a two-stage filter device comprising one or more non-vertical walls in a method described herein or other methods, the diameters of the upper and lower parts of the first container are not critical. Respective diameters of the upper and lower parts of the first container may be chosen by one of ordinary skill in the art depending, e.g., on the size of tissue sample to be processed and other parameters in view of the description herein. In some embodiments wherein the first container comprises one or more non-vertical walls, the upper part of the first container may have a diameter ranging from about 5 mm to about 150 mm, preferably from about 10 mm to about 100 mm, more preferably from about 13 mm to about 50 mm and most preferably from about 15 mm to about 30 mm and the lower part of the first container may have a diameter ranging from about 15 mm to about 200 mm, preferably from about 20 mm to about 100 mm, more preferably from about 25 mm to about 75 mm and most preferably from about 30 mm to about 50 mm.

For using a two-stage filter device comprising one or more non-vertical walls in a method described herein or other methods, the walls of the first container may be arranged at different angles with respect to each other. The angles are not critical. Respective angles of the walls of the first container may be chosen by one of ordinary skill in the art depending, e.g., on the size of tissue sample to be processed and other parameters in view of the description herein. In some embodiments wherein the first container comprises one or more non-vertical walls, the walls may be arranged at an angle ranging from about 30 to about 60 degree, preferably from about 30 to about 55 degree, more preferably from about 30 to about 50 degree, and most preferably from about 30 to about 45 degree.

The height of the first container can also vary. For using a two-stage filter device in a method described herein or other methods, the height of the first container is not critical. A certain height of the first container may be chosen by one of ordinary skill in the art depending, e.g., on the size of tissue sample to be processed and other parameters in view of the description herein. In some embodiments, the height of the first container ranges from about 20 mm to about 300 mm, preferably from about 25 mm to about 200 mm, more preferably from about 40 mm to about 100 mm and most preferably from about 50 to about 75 mm.

A first container comprises a first wall shown schematically as 4 in the Figures herein. As will be understood, depending on the shape of the first container, the first container may have more than one first wall. For example, a rectangular first container has four first walls and a hexagonal first container has six first walls. At least one first wall of the first container is permeable for cell culture medium, for single cells and for cell aggregates. Single cells and cell aggregates may be prepared from a tissue sample as described herein. In embodiments wherein the first container is a cylindrical container, the first container may be permeable across the entire cylindrical container or only parts thereof.

The permeability of the first container is determined by a first plurality of pores present in a first wall, more specifically by the sizes of the pores of the first plurality of pores. A first plurality of pores is shown schematically as 7 in the Figures herein. Thus, in some embodiments, a first wall 4 of a first container 1 comprises a first plurality of pores 7. Essentially, the pores of the first plurality of pores are large enough to allow single cells (indicated as 16 in FIG. 4) and cell aggregates (indicated as 17 in FIG. 4) to pass through and small enough to not allow a tissue biopsy sample (indicated as 15 in FIG. 4) or tissue fragments having more than 200 cells to pass through.

Rather elongated tissue fragments prepared from a tissue sample may, however, still pass through pores of the first plurality of pores. It is an objective of the present invention to provide a two-stage filter device wherein only a minority, rather than a majority of the tissue fragments pass through the pores of the first plurality of pores, while a majority of single cells and cell aggregates pass through the pores of the first plurality of pores. Typically, less than 50% of tissue fragments pass through the pores of the first plurality of pores. In some embodiments, less than 40% of tissue fragments pass through the pores of the first plurality of pores. In some embodiments, less than 35% of tissue fragments pass through the pores of the first plurality of pores. In some embodiments, less than 30% of tissue fragments pass through the pores of the first plurality of pores. In some embodiments, less than 25% of tissue fragments pass through the pores of the first plurality of pores. In some embodiments, less than 20% of tissue fragments pass through the pores of the first plurality of pores. In some embodiments, less than 15% of tissue fragments pass through the pores of the first plurality of pores. In some embodiments, less than 10% of tissue fragments pass through the pores of the first plurality of pores. In some embodiments, less than 5% of tissue fragments pass through the pores of the first plurality of pores. In some embodiments, less than 2% of tissue fragments pass through the pores of the first plurality of pores. In some embodiments, less than 1% of tissue fragments pass through the pores of the first plurality of pores. Any tissue fragments that did not pass through the pores of the first plurality of pores can conveniently be collected from within the first container, e.g., by pipetting after settling on the bottom of the first container.

The pores in the first plurality of pores can be of any shape, such as rectangular, pentagonal, hexagonal, oval, or round. Preferred pores are round pores.

The first plurality of pores may have different size pores. For using a two-stage filter device in a method described herein or other methods, the pore size may be chosen by one of ordinary skill in the art depending, e.g., on the size of the tissue sample, the size of cell aggregates or tissue fragments to be prepared and other parameters in view of the description herein. In some embodiments, the first plurality of pores 7 comprises pores having substantially the same size pores. In some embodiments, the size of the pores in the first plurality of pores ranges from about 10 μm to about 2,000 μm, preferably from about 20 μm to about 1,000 μm, more preferably from about 30 μm to about 500 μm and most preferably from about 50 μm to about 200 μm. In some embodiments, the first plurality of pores comprises pores having different size pores.

In some embodiments, the first plurality of pores 7 comprises pores ranging in size from about 50 μm to about 100 μm, from about 100 μm to about 200 μm, from about 200 μm to about 300 μm, from about 300 μm to about 400 μm, from about 400 μm to about 500 μm, from about 500 μm to about 600 μm or from about 600 μm to about 1,000 μm.

The spatial arrangements of pores of the first plurality of pores 7 in the first wall 4 of the first container 1 may vary. In some embodiments, the pores of the first plurality of pores are arranged in a regular patter, e.g., in lines such that one pore is located on top of another pore or one pore is located to the left or right of another pore on a line. Such regular horizontal and vertical arrangement of pores is schematically depicted in FIG. 5A. Alternatively, the pores can be arranged in vertical lines and horizontally offset or in horizontal lines and vertically offset (FIG. 5B). The pores of the first plurality of pores can also be arranged in an irregular or random pattern (FIG. 5C). While FIGS. 5A-C schematically depict same size pores, each first wall may comprise different size pores arranged as shown exemplary in FIG. 5D. The shape of pores of the first plurality of pores 7 in the first wall 4 of the first container 1 may also vary. While FIGS. 5A-D schematically depict round pores, each first wall may comprise different shaped pores, e.g., as shown exemplary in FIG. 5E. The pattern of the pores can be random or non-random.

The first wall of the first container may be of various thickness. For using a two-stage filter device in a method described herein or other methods, the thickness of the first wall may be chosen by one of ordinary skill in the art depending, e.g., on the size of the tissue sample, the size of cell aggregates to be prepared and other parameters in view of the description herein. In some embodiments, the thickness of the first wall ranges from about 0.1 mm to about 5 mm, preferably from about 0.2 mm to about 4 mm, more preferably from about 0.3 mm to about 2 mm and most preferably from about 0.5 mm to about 1 mm.

The first container can be made of various materials. Essentially many materials can be used. A preferred material is a material to which the cells or cell aggregates substantially do not adhere. Suitable materials include, but are not limited to stainless steel, polypropylene, nylon, polytetrafluoroethylene and polystyrene. A preferred material is stainless steel.

ii. Second Container

In some embodiments of the present invention a device for processing a tissue sample to prepare a plurality of cells, a plurality of cell aggregates and/or tissue fragments comprises a second container. A second container within a two-stage filter device is shown schematically as 2 in the Figures herein. Typically the first container 1 is nested in the second container 2 as shown schematically in FIGS. 1-4, 6, and 7.

The shape and size of the second container can vary according to the use and volume of sample being processed as described herein. A shape and size of the second container may be chosen by one of ordinary skill in the art depending, e.g., on the shape and size of the first container and in view of the description herein. In some embodiments, the second container is a cylindrical container. An exemplary arrangement of a cylindrical second container in a two-stage filter is shown schematically in FIG. 2A. In some embodiments, the second container is an oval container. An exemplary arrangement of an oval second container in a two-stage filter device is shown schematically in FIG. 2B. In some embodiments, the second container is a rectangular container. An exemplary arrangement of a rectangular second container in a two-stage filter device is shown schematically in FIGS. 2C and 2E. In some embodiments, the second container is a container having four, five, six or more sides. An exemplary arrangement of a hexagonal second container in a two-stage filter device is shown schematically in FIGS. 2D and 2F.

Preferably, the shape of the second container is a shape that is substantially the same as the shape of first container, which is nested in the second container. Thus, in some embodiments, the first and second container have the same shape. In such embodiments, the spacing between the walls of the first and second containers can be substantially the same. This, however, must not be the case. As long as the first container can be nested into the second container, the first and second container can be of different shape. For example a cylindrical first container can be nested in an oval second container. Likewise a cylindrical first container can be nested into a hexagonal second container, a hexagonal first container can be nested in a cylindrical second container, etc. Thus, in some embodiments, the shape of a first container is different than the shape of a second container (e.g., see FIGS. 2E and 2F).

In some embodiments, a second container comprises substantially vertical walls. For using a two-stage filter device in a method described herein or other methods, the diameter of the second container is not critical. A certain diameter of the second container may be chosen by one of ordinary skill in the art depending, e.g., on the diameter of the first container and other parameters in view of the description herein. In some embodiments wherein the second container comprises substantially vertical walls, the second container has a diameter ranging from about 10 mm to about 200 mm, preferably from about 15 mm to about 100 mm, more preferably from about 20 mm to about 50 mm and most preferably from about 20 mm to about 35 mm. As one of ordinary skill in the art will appreciate within the context of a two-stage filter device described herein, the diameter of the second container is larger than the diameter of the first container.

In some embodiments, a second container comprises one or more non-vertical walls. A non-vertical wall, e.g., is a wall arranged at an angle. In some embodiments, the upper part of the second container is narrower than the lower part of the second container. An exemplary embodiment of a two-stage filter wherein the upper part of the second container is narrower than the lower part of the second container is schematically shown in FIG. 3.

For using a two-stage filter device comprising one or more non-vertical walls in a method described herein or other methods, the diameters of the upper and lower parts of the second container are not critical. Respective diameters of the upper and lower parts of the second container may be chosen by one of ordinary skill in the art depending, e.g., on the diameter of upper and lower parts of the first container and other parameters in view of the description herein. In some embodiments wherein the second container comprises one or more non-vertical walls, the upper part of the second container may have a diameter ranging from about 10 mm to about 200 mm, preferably from about 15 mm to about 100 mm, more preferably from about 15 mm to about 50 mm and most preferably from about 20 mm to about 35 mm and the lower part of the second container may have a diameter ranging from about 20 mm to about 250 mm, preferably from about 25 mm to about 200 mm, more preferably from about 30 mm to about 100 mm and most preferably from about 40 mm to about 70 mm.

For using a two-stage filter device comprising one or more non-vertical walls in a method described herein or other methods, the walls of the second container may be arranged at different angles with respect to each other. The angles are not critical. Respective angles of the walls of the second container may be chosen by one of ordinary skill in the art depending, e.g., on the angles of the walls of the first container and other parameters in view of the description herein. In some embodiments wherein the second container comprises one or more non-vertical walls, the one or more walls may be arranged at an angle ranging from about 30 to about 60 degree, preferably from about 30 to about 55 degree, more preferably from about 30 to about 50 degree and most preferably from about 30 to about 45 degree.

Figure 4:
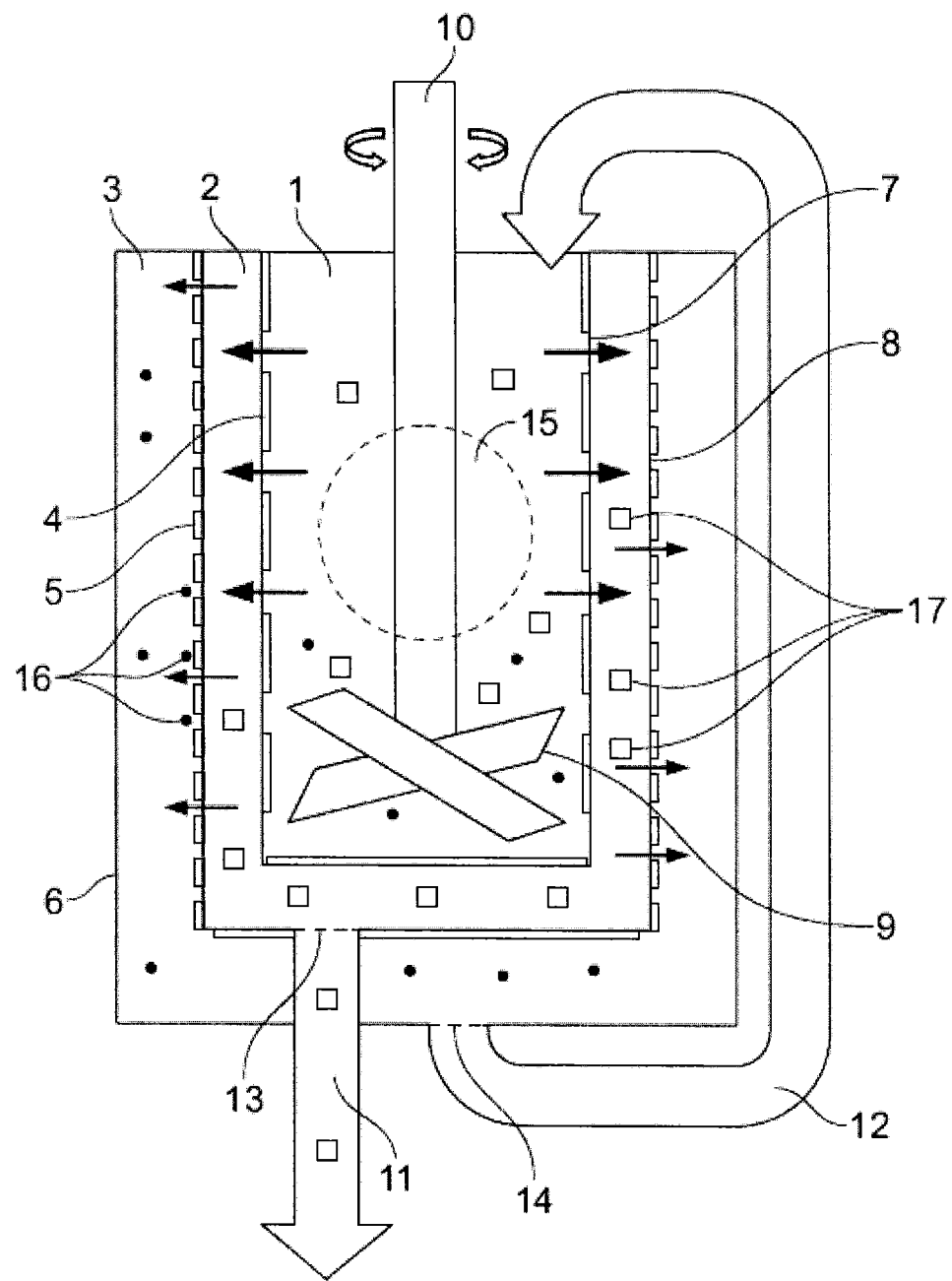
FIG. 4 schematically depicts the distribution of single cells, cell aggregates and tissue fragments in an exemplary two-stage filter device during and after processing of a tissue sample 15 (indicated by interrupted circle). Single cells 16 (indicated by black dots) and cell aggregates 17 (indicated by open squares) are located in the first container 1 and can pass through the first plurality of pores 7 into the second container 2. While single cells 16 can pass through the second plurality of pores 8, tissue fragments and cell aggregates 17 cannot. Tissue fragments and cell aggregates 17 may be collected through a collection channel 11 after opening of gate 13. Containers 1, 2, and 3 may be open or closed at the top (as indicated by a solid line). The description of parts is as in FIG. 1 and as described herein.

The height of the second container can also vary. For using a two-stage filter device in a method described herein or other methods, the height of the second container is not critical. A certain height of the second container may be chosen by one of ordinary skill in the art depending, e.g., on the height of the first container and other parameters in view of the description herein. In some embodiments, the height of the second container ranges from about 50 mm to about 300 mm, preferably from about 50 mm to about 200 mm, more preferably from about 50 mm to about 100 mm and most preferably from about 50 to about 75 mm. In some embodiments of a two stage filter device, when measured from the bottom of the respective first and second containers, the height of the second container is larger than the height of the first container (e.g., as schematically depicted in FIGS. 1, 3, and 4). Preferably, the height of the second container is such that its upper end is substantially flush with the upper end of the first container. This ensures that a single lid 19 (FIG. 7) can be used to cover the upper openings of the first and second containers. In some embodiments of methods described herein, it is desirable to cover the upper openings of the containers with a lid to protect the cell culture medium, cells and cell aggregates from becoming contaminated.

A second container comprises a second wall shown schematically as 5 in the Figures herein. As will be understood, depending on the shape of the second container, the second container may have more than one second wall. For example, a rectangular second container has four second walls and a hexagonal second container has six second walls. At least one second wall of the second container is permeable for cell culture medium and for single cells and substantially not permeable for cell aggregates. Single cells and cell aggregates may be prepared from a tissue sample as described herein. In embodiments wherein the second container is a cylindrical container, the second container may be permeable for cell culture medium and single cells across the entire cylindrical container or only parts thereof.

The passage of cells or very small cell aggregates (e.g., cell aggregates of 2-5 cells) through the second wall of the second container is determined by a second plurality of pores present in a second wall, more specifically by the sizes of the pores of the second plurality of pores. A second plurality of pores is shown schematically as 8 in the Figures herein. Thus, in some embodiments, a second wall of a second container comprises a second plurality of pores. Essentially, the pores of the second plurality of pores are large enough to allow single cells (indicated as 15 in FIG. 4) to pass through and small enough to not allow cell aggregates (indicated as 16 in FIG. 4) and tissue fragments to pass through.

Rather elongated cell aggregates may, however, still pass through pores of the second plurality of pores. It is an objective of the present invention to provide a two-stage filter device wherein only a minority, rather than a majority of the cell aggregates pass through the pores of the second plurality of pores, while a majority of single cells which passed through the pores of the first plurality of pores pass through the pores of the second plurality of pores. Typically, less than 50% of cell aggregates which passed through the pores of the first plurality of pores pass through the pores of the second plurality of pores. In some embodiments, less than 40% of cell aggregates which passed through the pores of the first plurality of pores pass through the pores of the second plurality of pores. In some embodiments, less than 35% of cell aggregates which passed through the pores of the first plurality of pores pass through the pores of the second plurality of pores. In some embodiments, less than 30% of cell aggregates which passed through the pores of the first plurality of pores pass through the pores of the second plurality of pores. In some embodiments, less than 25% of cell aggregates which passed through the pores of the first plurality of pores pass through the pores of the second plurality of pores. In some embodiments, less than 20% of cell aggregates which passed through the pores of the first plurality of pores pass through the pores of the second plurality of pores. In some embodiments, less than 15% of cell aggregates which passed through the pores of the first plurality of pores pass through the pores of the second plurality of pores. In some embodiments, less than 10% of cell aggregates which passed through the pores of the first plurality of pores pass through the pores of the second plurality of pores. In some embodiments, less than 5% of cell aggregates which passed through the pores of the first plurality of pores pass through the pores of the second plurality of pores. In some embodiments, less than 2% of cell aggregates which passed through the pores of the first plurality of pores pass through the pores of the second plurality of pores. In some embodiments, less than 1% of cell aggregates which passed through the pores of the first plurality of pores pass through the pores of the second plurality of pores.

The pores in the second plurality of pores can be of any shape, such as rectangular, pentagonal, hexagonal, oval, or round. Preferred pores are round pores.

The second plurality of pores may have different size pores. For using a two-stage filter device in a method described herein or other methods, the pore size may be chosen by one of ordinary skill in the art depending, e.g., on the size of the tissue sample, the size of cell aggregates to be prepared, the size of pores within the first plurality of pores in the first wall of the first container and other parameters in view of the description herein. In some embodiments, the second plurality of pores comprises pores having substantially the same size pores. In some embodiments, the size of the pores in the second plurality of pores ranges from about 10 μm to about 200 μm, preferably from about 20 μM to about 150 μm, more preferably from about 25 μm to about 100 μm and most preferably from about 30 μm to about 50 μm. In some embodiments, the second plurality of pores comprises pores having different size pores. As one of ordinary skill in the art will appreciate, within the context of the two-stage filter device described herein the pores of the second plurality of pores are smaller in size than the pores of the first plurality of pores.

The spatial arrangements of pores of the second plurality of pores in the second wall of the second container may vary. In some embodiments, the pores of the second plurality of pores are arranged in a regular patter, e.g., in lines such that one pore is located on top of another pore or one pore is located to the left or right of another pore on a line. Such regular horizontal and vertical arrangement of pores is schematically depicted in FIG. 5A. Alternatively, the pores can be arranged in vertical lines and horizontally offset or in horizontal lines and vertically offset (FIG. 5B). The pores of the second plurality of pores can also be arranged in an irregular or random pattern (FIG. 5C). While FIGS. 5A-C schematically depict same size pores, each second wall may comprise different size pores as shown exemplary in FIG. 5D. The shape of pores of the second plurality of pores 8 in the second wall 5 of the second container 2 may also vary. While FIGS. 5A-D schematically depict round pores, each second wall may comprise different shaped pores, e.g., as shown exemplary in FIG. 5E. The pattern of the pores can be random or non-random.

A second wall of a second container may be of various thickness. For using a two-stage filter device in a method described herein or other methods, the thickness of the second wall may be chosen by one of ordinary skill in the art depending, e.g., on the size of the tissue sample, the size of cell aggregates to be prepared and other parameters in view of the description herein. In some embodiments, the thickness of a second wall ranges from about 0.1 mm to about 5 mm, preferably from about 0.2 mm to about 3 mm, more preferably from about 0.3 mm to about 4 mm and most preferably from about 0.5 mm to about 1 mm.

The second container can be made of various materials. Essentially many materials can be used for a second container. A preferred material for a second container is a material to which cells or cell aggregates substantially do not adhere. Suitable materials include, but are not limited to stainless steel, polypropylene, nylon, polytetrafluoroethylene, and polystyrene. A preferred material is stainless steel. The first and second containers may be made of the same material. In some embodiments, the material for the first container is different from the material of the second container.

As described herein, the first container is nested within the second container. As schematically shown in FIGS. 1-4 and 6-7, the first walls of the first container and the second walls of the second container are spaced apart. The spacing between those walls can vary. For using a two-stage filter device in a method described herein or other methods, the spacing between the first wall of the first container and the second wall of the second container may be chosen by one of ordinary skill in the art depending, e.g., on the size of the tissue sample, the size of cell aggregates to be prepared and other parameters in view of the description herein. In some embodiments, the spacing between a first wall and a second wall ranges from about 2 mm to about 100 mm, preferably from about 5 mm to about 50 mm, more preferably from about 7 mm to about 45 mm and most preferably from about 10 mm to about 30 mm. As schematically depicted in FIGS. 1-4 and 6-7, the spacing between the first walls and the second walls is substantially the same, i.e., substantially the same with respect to the vertical, horizontal or non-vertical dimensions of the two containers. However, the spacing between the first walls and second walls can be substantially different so that the spacing between the bottom first wall of the first container and bottom second wall of the second container is less or more than the spacing between a first side wall (vertical or non-vertical wall) of the first container and the second side wall (vertical or non-vertical wall) of the second container.

Optionally, the second container comprises a collection channel, which is indicated by 11 in the Figures herein. The collection channel is particularly useful for collecting cell aggregates that passed through the pores of the first plurality of pores, but not through the second plurality of pores. Preferably, the collection channel is located at the bottom of the second container. The shape and form of the collection channel is not limited. Without limitation, a collection channel can be in the form of a tube or a fennel. Cell aggregates collected through the collection channel can be used in a variety of applications as described herein. Cell aggregates collected through the collection channel can also be frozen for later use.

Further, optionally passage of the cell aggregates through the collection channel may be controlled by a gate 13. When the gate is closed, cell aggregates cannot pass through the collection channel. When the gate is open, cell aggregates can pass through the collection channel and can be collected. A gate at a collection channel for cell aggregates is schematically depicted as 13 in the Figures herein.

iii. Third Container

In some embodiments of the present invention a device for processing a tissue sample to prepare a plurality of cells, a plurality of cell aggregates and/or tissue fragments comprises a third container. A third container within a two-stage filter device is shown schematically as 3 in the Figures herein. Typically the second container 2 is nested in the third container 3 as shown schematically in FIGS. 1-4, and 6-7.

The shape and size of the third container can vary according to the use and volume of sample being processed as described herein. A shape and size of the second container may be chosen by one of ordinary skill in the art depending, e.g., on the shape and size of the first or second containers and in view of the description herein. In some embodiments, the third container is a cylindrical container. An exemplary arrangement of a cylindrical third container in a two-stage filter is shown schematically in FIG. 2A. In some embodiments, the third container is an oval container. An exemplary arrangement of an oval third container in a two-stage filter device is shown schematically in FIG. 2B. In some embodiments, the third container is a rectangular container. An exemplary arrangement of a rectangular third container in a two-stage filter device is shown schematically in FIGS. 2C and 2E. In some embodiments, the third container is a container having four, five, six or more sides. An exemplary arrangement of a hexagonal third container in a two-stage filter device is shown schematically in FIGS. 2D and 2F.

Preferably, the shape of the third container is a shape that is substantially the same as the shape of second container, which is nested into the third container. Thus, in some embodiments, the second and third container have the same shape. In such embodiments, the spacing between the walls of the second and third containers can be substantially the same. This, however, must not be the case. As long as the second container can be nested into the third container, the second and third container can be of different shape. For example a cylindrical second container can be nested in an oval third container. Likewise a cylindrical second container can be nested into a hexagonal third container, a hexagonal second container can be nested in a cylindrical third container, etc. Thus, in some embodiments, the shape of a second container is different than the shape of a third container.

In some embodiments, a third container comprises substantially vertical walls. For using a two-stage filter device in a method described herein or other methods, the diameter of the third container is not critical. A certain diameter of the third container may be chosen by one of ordinary skill in the art depending, e.g., on the diameter of the first and/or second containers and other parameters in view of the description herein. In some embodiments, wherein the third container comprises substantially vertical walls, the third container has a diameter ranging from about 15 mm to about 250 mm, preferably from about 20 mm to about 200 mm, more preferably from about 30 mm to about 100 mm and most preferably from about 35 mm to about 50 mm. As one of ordinary skill in the art will appreciate within the context of a two-stage filter device described herein, the diameter of the third container is larger than the diameter of the first and second containers.

In some embodiments, a third container comprises one or more non-vertical walls. A non-vertical wall, e.g., is a wall arranged at an angle. In some embodiments, the upper part of the third container is narrower than the lower part of the third container. An exemplary embodiment of a two-stage filter wherein the upper part of the third container is narrower than the lower part of the third container is schematically shown in FIG. 3.

For using a two-stage filter device comprising one or more non-vertical walls in a method described herein or other methods, the diameters of the upper and lower parts of the third container are not critical. Respective diameters of the upper and lower parts of the third container may be chosen by one of ordinary skill in the art depending, e.g., on the diameter of upper and lower parts of the first and/or second containers and other parameters in view of the description herein. In some embodiments wherein the third container comprises one or more non-vertical walls, the upper part of the second container may have a diameter ranging from about 15 mm to about 250 mm, preferably from about 20 mm to about 200 mm, more preferably from about 30 mm to about 100 mm and most preferably from about 35 mm to about 50 mm and the lower part of the third container may have a diameter ranging from about 30 mm to about 300 mm, preferably from about 40 mm to about 200 mm, more preferably from about 50 mm to about 100 mm and most preferably from about 60 mm to about 90 mm.

For using a two-stage filter device comprising one or more non-vertical walls in a method described herein or other methods, the walls of the third container may be arranged at different angles with respect to each other. The angles are not critical. Respective angles of the walls of the third container may be chosen by one of ordinary skill in the art depending, e.g., on the angles of the walls of the first and/or second containers and other parameters in view of the description herein. In some embodiments wherein the third container comprises one or more non-vertical walls, the one or more walls may be arranged at an angle ranging from about 30 to about 60 degree, preferably from about 30 to about 55 degree, more preferably from about 30 to about 50 degree, and most preferably from about 30 to about 45 degree.

The height of the third container can also vary. For using a two-stage filter device in a method described herein or other methods, the height of the third container is not critical. A certain height of the third container may be chosen by one of ordinary skill in the art depending, e.g., on the height of the first and/or second containers and other parameters in view of the description herein. In some embodiments, the height of the third container ranges from about 50 mm to about 300 mm, preferably from about 50 mm to about 200 mm, more preferably from about 50 mm to about 100 mm and most preferably from about 50 to about 75 mm. In some embodiments of a two stage filter device, when measured from the bottom of the respective second and third containers, the height of the third container is larger than the height of the second container (e.g., as schematically depicted in FIGS. 1, 3, and 4). Preferably, the height of the third container is such that its upper end is substantially flush with the upper end of the first container. This ensures that a single lid 19 (FIG. 7) can be used to cover the upper openings of the second and third containers. In some embodiments of methods described herein, it is desirable to cover the upper openings of the containers with a lid to protect the cell culture medium, cells and cell aggregates within a device from becoming contaminated.

A third container comprises a third wall shown schematically as 6 in the Figures herein. As will be understood, depending on the shape of the third container, the third container may have more than one third wall. For example, a rectangular third container has four third walls and a hexagonal third container has six third walls. While walls of the first and second containers are permeable for cell aggregates and/or single cells, the third walls do not exhibit such permeability.

A third wall of the third container may be of various thickness. For using a two-stage filter device in a method described herein or other methods, the thickness of the third wall may be chosen by one of ordinary skill in the art depending, e.g., on the size of the tissue sample, the size of cell aggregates to be prepared and other parameters in view of the description herein. In some embodiments, the thickness of a third wall ranges from about 0.1 mm to about 5 mm, preferably from about 0.2 mm to about 4 mm, more preferably from about 0.3 mm to about 2 mm and most preferably from about 0.5 mm to about 1 mm.

The third container can be made of various materials. Essentially many materials can be used for a third container. A preferred material for a third container is a material to which cells or cell aggregates substantially do not adhere. Suitable materials include, but are not limited to stainless steel, polypropylene, nylon, and polystyrene. A preferred material is Stainless steel. The materials for the first, second, and third containers can be the same or different.

As described herein, the second container is nested within the third container. As schematically shown in FIGS. 1-4 and 6-7, the second walls of the second container and the third walls of the third container are spaced apart. The spacing between those walls can vary. For using a two-stage filter device in a method described herein or other methods, the spacing between the second wall of the second container and the third wall of the third container may be chosen by one of ordinary skill in the art depending, e.g., on the size of the tissue sample, the size of cell aggregates to be prepared and other parameters in view of the description herein. In some embodiments, the spacing between a second wall and a third wall ranges from about 2 mm to about 100 mm, preferably from about 5 mm to about 75 mm, more preferably from about 7 mm to about 50 mm and most preferably from about 10 mm to about 30 mm. As schematically depicted in FIGS. 1-4 and 6-7, the spacing between the second walls and the third walls is substantially the same, i.e., substantially the same with respect to the vertical, horizontal or non-vertical dimensions of the two containers. However, the spacing between the second walls and third walls can be substantially different so that the spacing between the bottom second wall of the second container and bottom third wall of the third container is less or more than the spacing between a second side wall (vertical or non-vertical wall) of the second container and a third side wall (vertical or non-vertical wall) of the third container.

Optionally, the third container comprises a channel tube, which is indicated by 12 in the Figures herein. The channel tube is particularly useful for transporting cell culture medium, single cells, and very small cell aggregates that passed through the pores of the first plurality of pores and through the second plurality of pores back into the first container. Preferably, the channel tube is located at the bottom of the third container. It may also be located at a side wall of the third container. The shape and form of the channel tube is not limited.

Further, optionally transporting the cell culture medium and single cells through the collection tube back into the first container may be controlled by a gate 14. When gate 14 is closed, no transportation of cell culture medium, single cells and/or very small cell aggregates (e.g., cell aggregates of 2-5 cells) takes place. When gate 14 is open, transportation of cell culture medium, single cells, and/or very small cell aggregates can take place. In some embodiment, the channel tube is connected to a pump. In some embodiments, an additional filter is placed at gate 14 to allow the passage of fluid or cell culture medium through channel 12 without allowing passage of cells and/or very small cell aggregates (e.g., cell aggregates of 2-5 cells). After transporting the fluid or cell culture medium (with or without single cells and/or very small cell aggregates) through channel 12, the fluid or cell culture medium (with or without single cells and/or very small cell aggregates) can be introduced back into the first container 1 through an inlet 18 (e.g., see FIG. 7).

iv. Cutting Blade

In some embodiments of the present invention a device for processing a tissue sample to prepare a plurality of cells, a plurality of cell aggregates and/or tissue fragments comprises a cutting blade 9. In some embodiments of the present invention a device for processing a tissue sample to prepare a plurality of cells and a plurality of cell aggregates comprises a plurality of cutting blades 9. As described herein, a cutting blade 9 can have different forms, shapes, and dimensions. Further, as described herein, individual members of the plurality of cutting blades 9, can have different forms, shapes, and dimensions and can be arranged in various configurations with respect to each other. Typically, within a two-stage filter device, the cutting blade 9 resides within the first container 1 as shown schematically in FIGS. 1, 3-4, and 6-7. A cutting blade 9 comprises at least one sharp edge, which points into the interior part of a container into which a tissue sample will be placed and with which the cutting blade 9 contacts the tissue sample for processing and preparing of plurality of cells, cell aggregates and/or tissue fragments.

The function of the cutting blade essentially is to process a tissue sample so that a plurality of single cells, a plurality of cell aggregates and/or tissue fragments can be obtained therefrom.

Various cutting blade configurations are provided herein. In some embodiments of the present invention, a cutting blade 9 is attached to a cutting rotation shaft 10 as is schematically shown in FIGS. 1, 3-4, and 6-7. In this embodiment, the cutting blade and part or all of the rotation shaft extend into the interior of the first container. A plurality of blades 9 may be attached to a single shaft 10. In this embodiment of a two-stage filter device, a first blade 9 may be attached to substantially the same position at a shaft 10, where a second blade 9 is attached, e.g., as schematically shown in FIGS. 1, 3, 4, and 6-7. Alternatively, a second blade 9 may be attached to a shaft 10 at a position, which is on top of the position to which a first blade 9 is attached to the shaft 10. In some embodiments, a plurality of blades is attached to a shaft at a plurality of positions at the shaft 10. Attaching a plurality of blades 9 to a shaft 10 at a plurality of positions ensures that a tissue sample will be in contact with a blade 9 more often and be processed more efficiently compared to a similar device having only a single blade 9.

In some embodiments, a cutting blade is attached to the bottom of a first container. The attachment of the cutting blade to the bottom of the first container, preferably is permanent. However, the attachment can also be temporarily, e.g., for a time needed to process a tissue sample.

In some embodiments, a cutting blade is disposed adjacent to the bottom of a first container.

As described above, the function of the cutting blade, when activated, is to process a tissue sample so that smaller parts thereof, such as tissue fragments, cell aggregates and single cells can be obtained. In some embodiments, the processing of a tissue sample is achieved by a rotating blade. Thus, in some embodiments, a cutting blade is rotatable. In some embodiments, a cutting blade is configured to process a tissue sample by rotating the blade while in contact with the tissue sample in the first container. As such, the processing operation is accomplished by the rotation of the cutting blade.

Using a two-filter device described herein, a user makes use of rotational force to process a tissue sample and to move cell aggregates and/or tissue fragments through the plurality of pores within the first wall of the first container and within the second, wall of the second container. When a user activates a two-filter device the user also sets the rotational speed of the shaft/cutting blade(s) at a desired level. The rotational speed can vary. The slower the rotational speed, and hence the rotational force applied to the tissue sample, cell aggregates, and tissue fragments, the longer it will take to mince a tissue sample and to move the cell aggregates and/or tissue fragments through the pores. However, the slower the rotational speed, the more cells might be viable. Thus, preferably, low rotational speed is being applied. In some embodiments, low rotational speed comprises ranges from about 50 rpm to about 200 rpm, from about 100 rpm to about 500 rpm, from about 200 rpm to about 1,000 rpm, and from about 500 rpm to about 2,000 rpm. In some embodiments, high rotational speed is being applied. In some embodiments, high rotational speed comprises ranges from about 2,000 rpm to about 3,000 rpm, from about 3,000 rpm to about 5,000 rpm, from about 5,000 rpm to about 10,000 rpm. The rotational force allows contacting the tissue sample with a cutting blade so that when the tissue sample makes contact with the cutting blade it is minced into smaller parts, such as cell aggregates and tissue fragments, which then, depending on the size of pores pass or don't pass through those. The majority of cell aggregates then passes through the pores of the first plurality of pores into the second container from where they can be collected. In some embodiments, the rotational force is increased during the processing of the tissue sample to ensure that the tissue sample once contacted to a cutting blade is processed completely.

Once tissue fragments, cell aggregates and single cells are released from the tissue sample, during the processing operation, the cutting blade efficiently stirs the mixture of cell culture medium, tissue fragments, cell aggregates and single cells. Essentially, a rotational or centrifugal force is applied moving the single cells, cell aggregates and tissue fragments towards the first wall of the first container and towards the first plurality of pores within the first wall of the first container. Single cells and cell aggregates (and a few tissue fragments) will be moved through the pores of the first plurality of pores, while larger cell conglomerates and larger tissue fragments will not. Larger cell conglomerates and tissue fragments are prevented from adhering to the first walls of the first container. Upon completion of the processing, the processed tissue, preferably, is of substantially uniform size. As described herein, the speed of the rotating blade can be controlled to assure a desirable ratio of tissue fragments to cell aggregates to single cells can be obtained.

Different means can be used to rotate a cutting blade attached to a rotating shaft. In some embodiments the rotating shaft is communicatively coupled to a motorized unit. In some embodiments, a motorized unit comprises a blade rotating motor. In some embodiments, a motorized unit comprises a controller. The controller controls several functions. For example, the controller controls the blade rotating motor. In some embodiments, a motorized unit comprises a means for alternatively lowering and raising the cutting blade. The lowering and raising of the cutting blade thus ensures that the cutting blade will be in contact with the tissue sample, irrespective of the location of the tissue sample in the first container. The lowering and raising of the cutting blade can also be controlled by the controller. The controller also allows the cutting blade to move from a first position, e.g., close to the bottom of the first container, to a second position, e.g., to an upper part within the first container. The controller further allows to move the cutting blade for a predetermined distance within the first container. In some embodiments, the controller also activates the cutting blade and, upon completion of processing, shuts it off.

The controller determines the speed of rotation of the blade. By controlling the speed of rotation of the cutting blade, it is possible to optimize the ratio of cell aggregates to single cells. As one of ordinary skill in the art will appreciate, the ratio of cell aggregates to single cells obtained at a given speed of rotation of the cutting blade also depends on the tissue sample.

In some embodiments, a cutting blade comprises a sharp edge at the side of contacting a tissue sample. This ensures better processing of the tissue sample to prepare a plurality of cells and a plurality of cell aggregates In some embodiments, the cutting blade processes a tissue sample by mechanical force.

In some embodiments, the cutting blade utilizes ultrasonic waves that generate vibrations with an ultrasonic transducer along a longitudinal axis of a cutting blade. Ultrasonic cutting blades and waveguides are known in the art.

A device for preparing cells when using a cutting blade, typically comprises a plurality of cutting blades. In some embodiments, the device comprises at least two cutting blades arranged together. In some embodiments, the device comprises at least three cutting blades arranged together. In some embodiments, the device comprises at least four cutting blades arranged together. The plurality of cutting blades is arranged in a way that the cutting blades extend radially from the center of rotation or from the rotating shaft to which they are attached. In some embodiments, the plurality of cutting blades is arranged in a way that the cutting blades extend radially at regular intervals from the center of rotation or from the rotating shaft to which they are attached. In some embodiments, the cutting blades are bent at different angles.

In a preferred embodiment, the device comprises four cutting blades arranged together. The four cutting blades can be arranged in the following exemplary arrangement: a first cutting blade is attached to a rotating shaft and is bent toward the bottom surface of the first container at an acute angle; a second cutting blade is provided on the opposite side of the first cutting blade at the rotating shaft and is bent toward the upper surface of the first container at an acute angle; a third cutting blade is provided between the first and second cutting blades at the rotating shaft and is bent toward the upper surface of the first container at a greater angle than the second cutting blade; and a fourth cutting blade is provided on the opposite side of the third cutting blade at the rotating shaft and is bent toward the upper surface of the first container at a greater angle than the third cutting blade. In this way, the first, second, third, and fourth cutting blades are configured to be bent at different angles and thus, are more effective in processing a tissue sample.

The shape of the cutting blade can vary. In some embodiments, a cutting blade is substantially rectangular in shape having a chamfered edge.

In some embodiments, a cutting blade 9 comprises a serrated edge with a plurality of sharp peaks. An exemplary embodiment of such cutting blade 9 is shown in FIG. 17. Tissue sample 15 will slide down the sharp and angled edges to yield cell aggregates of desired sizes. One of ordinary skill in the art will appreciate that each plurality of blades 9 or a single blade 9, as described herein in various configurations, may comprise a serrated edge with a plurality of sharp peaks.

2. Two-Membrane Device

As described above, it is an objective of the present invention to provide devices for processing a tissue sample to prepare a plurality of cells and a plurality of cell aggregates. More specifically, it is an objective of the present invention to provide devices that allow the preparation of cell aggregates and single cells from a tissue sample. In some embodiments of the present invention a device for processing a tissue sample to prepare cells and cell aggregates is a two-membrane device. In some embodiments of the present invention, a two-membrane device for processing a tissue sample to prepare cells and cell aggregates comprises one or more of the following: an arrangement of a first plurality of pores, an arrangement of a second plurality of pores. An exemplary embodiment of a two-membrane device for preparing cells is shown schematically in FIG. 8.

In some embodiments of the invention, a two-membrane device comprises two membranes, each membrane comprising differently sized pores. A two-membrane device can be is nested in a container.

In some embodiments of the present invention, a two-membrane device comprises a first wall, a second wall, a first bottom, and a second bottom. The first wall may also be referred to as inner wall and the second wall may also be referred to as outer wall.

In some embodiments of the present invention, a two-membrane device comprises a first plurality of pores 7. Suitable pores 7 (size, shape configuration, arrangement) within the first or inner wall include those described for the two-stage filter device herein.

In some embodiments of the present invention, a two-membrane device comprises a second plurality of pores 8. Suitable pores 8 (size, shape configuration, arrangement within the second or outer wall include those described for the two-stage filter device herein.

The two-membrane device can have characteristics with respect to form, shape weight, pore size substantially similar to those described herein for the first and second containers of the two-stage filter device. As one of ordinary skill in the art will appreciate the two-membrane device essentially functionally corresponds to the first and second containers of the two-stage filter device of FIGS. 1-7.

The two-membrane device may be molded in a single piece.

III. Systems

The present invention describes a variety of systems for processing a tissue sample to prepare a plurality of cells, a plurality of cell aggregates and/or tissue fragments comprising compositions and devices of the present invention.

In some embodiments, a system comprises a two-stage filter device and a tissue sample. A two-stage filter device and tissue samples have been fully described herein.

In some embodiments, a system comprises a two-membrane device and a tissue sample. A two-membrane device and tissue samples have been fully described herein.

The system described herein simplifies and streamlines the process of preparing cell aggregates or tissue fragments of a desired size from a tissue sample by using centrifugal forces, without the need for other complex electronics, feedback sensors or controlled flows other than the use of a centrifuge. Furthermore, the tissue, fluid and cutting device are within a closed system that reduces the risk for contamination that may occur in an open system that uses outside forces or pressure from flowing fluid.

IV. Methods

The present invention describes a variety of methods using compositions and devices of the invention.

A. Methods of Processing a Tissue to Prepare a Plurality of Cells, a Plurality of Cell Aggregates Cells and Tissue Fragments The present invention provides methods of processing a tissue sample to prepare a plurality of cells, a plurality of cell aggregates and/or tissue fragments from a tissue sample. In some embodiments, cells prepared from a tissue sample are a plurality of single cells. In some embodiments, cells prepared from a tissue sample are within a cell aggregate. In some embodiments, cells prepared from a tissue sample are within a tissue fragment. In some embodiments, cells prepared from a tissue sample comprise a plurality of single cells and cell aggregates. In some embodiments, cells prepared from a tissue sample comprise a plurality of single cells, cell aggregates and tissue fragments. In some embodiments, cells prepared from a tissue sample comprise cell aggregates and tissue fragments.

In some embodiments of the present invention, a method of processing a tissue sample to prepare a plurality of cells, a plurality of cell aggregates and/or tissue fragments comprises the step of selecting a tissue from which the plurality of cells, plurality of cell aggregates and/or tissue fragments can be prepared.

In some embodiments of the present invention, a method of processing a tissue sample to prepare a plurality of cells, a plurality of cell aggregates and/or tissue fragments comprises the step of providing a tissue from which the plurality of cells, plurality of cell aggregates and/or tissue fragments can be prepared.

In some embodiments of the present invention, a method of processing a tissue sample to prepare a plurality of cells, a plurality of cell aggregates and/or tissue fragments comprises the step of obtaining a tissue sample from a tissue from which the plurality of cells, plurality of cell aggregates and/or tissue fragments can be prepared.

In some embodiments of the present invention, a method of processing a tissue sample to prepare a plurality of cells, a plurality of cell aggregates and/or tissue fragments comprises the step of providing a device for placing in a tissue sample.

In some embodiments of the present invention, a method of processing a tissue sample to prepare a plurality of cells, a plurality of cell aggregates and/or tissue fragments comprises the step of placing a tissue sample into a device of the present invention, e.g., into a two-stage filter device or a two-membrane device.

In some embodiments of the present invention, a method of processing a tissue sample to prepare a plurality of cells, a plurality of cell aggregates and/or tissue fragments comprises the step of processing a tissue sample from which cells can be prepared. Upon processing the tissue sample, a processing mixture is generated comprising a plurality of single cells, a plurality of cell aggregates and/or tissue fragments.

In some embodiments of the present invention, a method of processing a tissue sample to prepare a plurality of cells, a plurality of cell aggregates and/or tissue fragments comprises the step of activating a device into which a tissue sample has been placed.

In some embodiments of the present invention, a method of processing a tissue sample to prepare a plurality of cells, a plurality of cell aggregates and/or tissue fragments comprises the step of adding an enzyme to a mixture comprising cell culture medium and a tissue sample. In some embodiments, the enzyme is selected from the group consisting of a DNAse, a lipase, a proteinase, collagenase, and trypsin.

In some embodiments of the present invention, a method of processing a tissue sample to prepare a plurality of cells, a plurality of cell aggregates and/or tissue fragments comprises the step of obtaining a sample from the processing mixture.

In some embodiments of the present invention, a method of processing a tissue sample to prepare a plurality of cells, a plurality of cell aggregates and/or tissue fragments comprises the step of analyzing a sample of the processing mixture for the presence of single cells, cell aggregates and/or tissue fragments.

In some embodiments of the present invention, a method processing a tissue sample to prepare a plurality of cells, a plurality of cell aggregates and/or tissue fragments comprises the step of analyzing a sample of the processing mixture for quantifying the number of single cells, cell aggregates and/or tissue fragments.

In some embodiments of the present invention, a method processing a tissue sample to prepare a plurality of cells, a plurality of cell aggregates and/or tissue fragments comprises the step of analyzing a sample of the processing mixture for determining the number of cells within a cell aggregate and/or tissue fragments.

In some embodiments of the present invention, a method of processing a tissue sample to prepare a plurality of cells, a plurality of cell aggregates and/or tissue fragments comprises the step of separating a cell aggregate from a plurality of single cells.

In some embodiments of the present invention, a method of processing a tissue sample to prepare a plurality of cells, a plurality of cell aggregates and/or tissue fragments comprises the step of separating a cell aggregate from tissue fragments.

In some embodiments of the present invention, a method of processing a tissue sample to prepare a plurality of cells, a plurality of cell aggregates and/or tissue fragments comprises the step of separating a plurality of cells from tissue fragments.

In some embodiments of the present invention, a method of processing a tissue sample to prepare a plurality of cells, a plurality of cell aggregates and/or tissue fragments comprises the step of collecting a cell aggregate.

In some embodiments of the present invention, a method of processing a tissue sample to prepare a plurality of cells, a plurality of cell aggregates and/or tissue fragments comprises the step of collecting a plurality of cells.

In some embodiments of the present invention, a method of processing a tissue sample to prepare a plurality of cells, a plurality of cell aggregates and/or tissue fragments comprises the step of collecting a tissue fragment.

As one of ordinary skill in the art will appreciate individual steps in the method for preparing a plurality of cells, a plurality of cell aggregates and/or tissue fragments described above can be practiced by more than one person, can be performed automatically, and can be performed in a different order. Further, not all steps described above are necessary to practice the method of processing a tissue sample to prepare a plurality of cells and a plurality of cell aggregates.

Further, as one of ordinary skill in the art will appreciate, cells, cell aggregates and tissue fragments prepared according to a subject method find use in various applications. Therefore, sterile handling procedures known to the skilled artisan should be used wherever possible.

1. Selecting and Providing a Tissue from which Single Cells, Cell Aggregates and/or Tissue Fragments can be Prepared One of skill in the art will appreciate that a wide variety of tissues can be used in the methods of the present invention. More specifically, a wide variety of tissues can be used in a method of processing a tissue sample to prepare a plurality of cells, a plurality of cell aggregates and/or tissue fragments. Suitable tissues for preparing single cells, cell aggregates and tissue fragments according to a method described herein include disease tissues and healthy tissues.

In some embodiments, a method of processing a tissue sample to prepare a plurality of cells, a plurality of cell aggregates and/or tissue fragments comprises the step of selecting a tissue comprising a neoplastic cell. In some embodiments, a method of processing a tissue sample to prepare a plurality of cells, a plurality of cell aggregates and/or tissue fragments comprises the step of providing a tissue comprising a neoplastic cell.

In some embodiments, a method of processing a tissue sample to prepare a plurality of cells, a plurality of cell aggregates and/or tissue fragments comprises the step of selecting a tissue comprising a malignant cell. In some embodiments, a method of processing a tissue sample to prepare a plurality of cells, a plurality of cell aggregates and/or tissue fragments comprises the step of providing a tissue comprising a malignant cell.

In some embodiments, a method of processing a tissue sample to prepare a plurality of cells, a plurality of cell aggregates and/or tissue fragments comprises the step of selecting a tissue comprising a cancerous cell. In some embodiments, a method of processing a tissue sample to prepare a plurality of cells, a plurality of cell aggregates and/or tissue fragments comprises the step of providing a tissue comprising a cancerous cell.

In some embodiments, a method of processing a tissue sample to prepare a plurality of cells, a plurality of cell aggregates and/or tissue fragments comprises the step of selecting a tissue comprising a precancerous cell. In some embodiments, a subject method comprises the step of providing a tissue comprising a precancerous cell.

In some embodiments, a method of processing a tissue sample to prepare a plurality of cells, a plurality of cell aggregates and/or tissue fragments comprises the step of selecting a tissue comprising a stem cell. In some embodiments, a method of processing a tissue sample to prepare a plurality of cells, a plurality of cell aggregates and/or tissue fragments comprises the step of providing a tissue comprising a stem cell.

In some embodiments, a method of processing a tissue sample to prepare a plurality of cells, a plurality of cell aggregates and/or tissue fragments comprises the step of selecting a tissue comprising a cancer stem cell. In some embodiments, a method of processing a tissue sample to prepare a plurality of cells, a plurality of cell aggregates and/or tissue fragments comprises the step of providing a tissue comprising a cancer stem cell.

In some embodiments, a method of processing a tissue sample to prepare a plurality of cells, a plurality of cell aggregates and/or tissue fragments comprises the step of selecting a tissue comprising a stem cell. In some embodiments, a method of processing a tissue sample to prepare a plurality of cells, a plurality of cell aggregates and/or tissue fragments comprises the step of providing a tissue comprising a stem cell.

In some embodiments, a method of processing a tissue sample to prepare a plurality of cells, a plurality of cell aggregates and/or tissue fragments comprises the step of selecting a tissue comprising an embryonic stem cell. In some embodiments, a method of processing a tissue sample to prepare a plurality of cells, a plurality of cell aggregates and/or tissue fragments comprises the step of providing a tissue comprising an embryonic stem cell.

In some embodiments, a method of processing a tissue sample to prepare a plurality of cells, a plurality of cell aggregates and/or tissue fragments comprises the step of selecting a tissue comprising a progenitor cell. In some embodiments, a method of processing a tissue sample to prepare a plurality of cells, a plurality of cell aggregates and/or tissue fragments comprises the step of providing a tissue comprising a progenitor cell.

Preferably, the tissue is a mammalian tissue. More preferably, the tissue is a primate tissue. Most preferably, the tissue is a human tissue.

i. Cancerous Tissue

One of ordinary skill in the art will appreciate that a wide variety of disease tissues from a subject can be used to prepare disease cells, disease cell aggregates and/or disease tissue fragments according to a subject method. A preferred disease tissue is a cancerous tissue. In some embodiments, a cancerous tissue is selected from the group consisting of a lung cancer tissue, a sarcoma tissue, a gastrointestinal cancer tissue, a genitourinary tract cancer tissue, a liver cancer tissue, a skin cancer tissue, a gynecological cancer tissue, a bone cancer tissue, a nervous system cancer tissue, a hematologic cancer tissue, and an adrenal gland cancer tissue.

a. Lung Cancer Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is a lung cancer tissue. A suitable lung cancer tissue includes, but is not limited to, bronchogenic carcinoma tissue [squamous cell tissue, undifferentiated small cell tissue, undifferentiated large cell tissue, adenocarcinoma tissue], alveolar [bronchiolar] carcinoma tissue, bronchial adenoma tissue, sarcoma tissue, lymphoma tissue, chondromatous hamartoma tissue, mesothelioma tissue, SCLC tissue, and NSCLC tissue.

b. Sarcoma Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is a sarcoma tissue. A suitable sarcoma tissue includes, but is not limited to, angiosarcoma tissue, fibrosarcoma tissue, rhabdomyosarcoma tissue, liposarcoma tissue, myxoma tissue, rhabdomyoma tissue, fibroma tissue, lipoma tissue and teratoma tissue.

c. Gastrointestinal Cancer Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is a gastrointestinal cancer tissue. A suitable gastrointestinal cancer tissue includes, but is not limited to, esophagus tissue [squamous cell carcinoma tissue, adenocarcinoma tissue, leiomyosarcoma tissue, lymphoma tissue], stomach cancer tissue [carcinoma tissue, lymphoma tissue, leiomyosarcoma tissue], pancreas cancer tissue [ductal adenocarcinoma tissue, insulinoma tissue, glucagonoma tissue, gastrinoma tissue, carcinoid tumor tissue, VIPoma tissue], small bowel cancer tissue [adenocarcinoma tissue, lymphoma tissue, carcinoid tumor tissue, Kaposi's sarcoma tissue, leiomyoma tissue, hemangioma tissue, lipoma tissue, neurofibroma tissue, fibroma tissue], and large bowel cancer tissue [adenocarcinoma tissue, tubular adenoma tissue, villous adenoma tissue, hamartoma tissue, leiomyoma tissue].

d. Genitourinary Tract Cancer Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is a genitourinary tract cancer tissue. A suitable genitourinary tract cancer tissue includes, but is not limited to kidney cancer tissue [adenocarcinoma tissue, Wilms tumor tissue (nephroblastoma tissue), lymphoma tissue, leukemia tissue, renal cell carcinoma tissue], bladder cancer tissue and urethra cancer tissue [squamous cell carcinoma tissue, transitional cell carcinoma tissue, adenocarcinoma tissue], prostate cancer tissue [adenocarcinoma tissue, sarcoma tissue], and testis cancer tissue [seminoma tissue, teratoma tissue, embryonal carcinoma tissue, teratocarcinoma tissue, choriocarcinoma tissue, sarcoma tissue, Leydig cell tumor tissue, fibroma tissue, fibroadenoma tissue, adenomatoid tumor tissue, lipoma tissue].

e. Liver Cancer Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is a liver cancer tissue. A suitable liver cancer tissue includes, but is not limited to, hepatocellular carcinoma tissue, cholangiocarcinoma tissue, hepatoblastoma tissue, angiosarcoma tissue, hepatocellular adenoma tissue, and hemangioma tissue.

f. Skin Cancer Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is a skin cancer tissue. A suitable skin cancer tissue includes, but is not limited to, malignant melanoma tissue, basal cell carcinoma tissue, squamous cell carcinoma tissue, Kaposi's sarcoma tissue, nevi tissue, dysplastic nevi tissue, lipoma tissue, angioma tissue, dermatofibroma tissue, keloid tissue, and psoriasis tissue.

g. Gynecological Cancer Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is a gynecological cancer tissue. A suitable gynecological cancer tissue includes, but is not limited to, cancer tissue of uterus [endometrial carcinoma tissue], cancer tissue of cervix [cervical carcinoma tissue, pre-invasive cervical dysplasia tissue], cancer tissue of ovaries [ovarian carcinoma tissue (serous cystadenocarcinoma tissue, mucinous cystadenocarcinoma tissue, endometrioid carcinoma tissue, clear cell adenocarcinoma tissue, unclassified carcinoma tissue), granulosa-theca cell tumor tissue, Sertoli-Leydig cell tumor tissue, dysgerminoma tissue, malignant teratoma tissue and other germ cell tumor tissues], cancer tissue of vulva [squamous cell carcinoma tissue, intraepithelial carcinoma tissue, adenocarcinoma tissue, fibrosarcoma tissue, melanoma tissue], cancer tissue of vagina [clear cell carcinoma tissue, squamous cell carcinoma tissue, sarcoma botryoides tissue (embryonal rhabdomyosarcoma tissue), and cancer tissue of fallopian tubes [carcinoma tissue].

h. Bone Cancer Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is a bone cancer tissue. A suitable bone cancer tissue includes, but is not limited to, osteogenic sarcoma tissue [osteosarcoma tissue], fibrosarcoma tissue, malignant fibrous histiocytoma tissue, chondrosarcoma tissue, Ewing's sarcoma tissue, malignant lymphoma tissue [reticulum cell sarcoma tissue], multiple myeloma tissue, malignant giant cell tumor tissue, chordoma tissue, osteochondroma tissue [osteocartilaginous exostoses tissue], benign chondroma tissue, chondroblastoma tissue, chondromyxoid fibroma tissue, osteoid osteoma tissue, and giant cell tumor tissue.

i. Nervous System Cancer Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is a nervous system cancer tissue. A suitable cancer tissue of the nervous system includes, but is not limited to skull cancer tissue [osteoma tissue, hemangioma tissue, granuloma tissue, xanthoma tissue, Paget's disease of bone tissue], meninges tissue [meningioma tissue, meningiosarcoma tissue, gliomatosis tissue], brain cancer tissue [astrocytoma tissue, medulloblastoma tissue, glioma tissue, ependymoma tissue, germinoma tissue (pinealoma tissue), glioblastoma multiforme tisue, oligodendroglioma tissue, schwannoma tissue, retinoblastoma tissue, congenital tumor tissue], and spinal cord cancer tissue [neurofibroma tissue, meningioma tissue, glioma tissue, sarcoma tissue].

j. Hematologic Cancer Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is a hematologic cancer tissue. A suitable hematologic cancer tissue includes, but is not limited to cancer tissue of blood [myeloid leukemia tissue (acute and chronic), acute lymphoblastic leukemia tissue, chronic lymphocytic leukemia tissue, myeloproliferative disease tissue, multiple myeloma tissue, myelodysplastic syndrome tissue], Hodgkin's disease tissue, and non-Hodgkin's lymphoma tissue (malignant lymphoma tissue). While typically for some of the hematologic cancers described above fluid samples are analyzed, those are also referred to as a "tissue" in the context of the present invention. Also within the meaning of a hematologic cancer tissue is a tissue from a subject having a hematologic malignancy. A hematologic malignancy includes any malignancy associated with cells in the bloodstream. Examples thereof include B and T cell lymphomas, leukemias including but not limited to low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia, chronic leukocytic leukemia, acute myelogenous leukemia, acute lymphoblastic leukemia, chronic lymphocytic leukemia, chronic myelogenous leukemia, lymphoblastic leukemia, lymphocytic leukemia, monocytic leukemia, myelogenous leukemia, and promyelocytic leukemia. It should be clear to those of skill in the art that these lymphomas will often have different names due to changing systems of classification (as previously discussed), and that patients having lymphomas and leukemias classified under different names may also benefit from the combined therapeutic regimens of the present invention.

k. Adrenal Gland Cancer Tissue

One of ordinary skill in the art will appreciate that a wide variety of cancerous tissues from a subject can be used to prepare cancer cells, cancer cell aggregates and/or cancer tissue fragments according to a subject method. A preferred cancerous tissue is an adrenal gland cancer tissue. A suitable adrenal gland cancer tissue includes, but is not limited to neuroblastoma tissue.

i. Disease Tissue

One of ordinary skill in the art will appreciate that a wide variety of disease tissues, other than cancerous tissues, from a subject can be used to prepare disease cells, disease cell aggregates and/or disease tissue fragments according to a subject method. In some embodiments, a disease tissue is selected from the group consisting of a cardiovascular disease tissue, an immune- or inflammation related disease tissue, an infectious disease tissue, and a neurologic disease tissue.

a. Cardiovascular Disease Tissue

One of ordinary skill in the art will appreciate that a wide variety of disease tissues from a subject can be used to prepare disease cells, disease cell aggregates and/or disease tissue fragments according to a subject method. A preferred disease tissue is a cardiovascular disease tissue. A suitable cardiovascular disease tissue, includes, but not is limited to, a tissue obtained from a subject having cardiac stun syndrome, myocardial infarction, congestive heart failure, stroke, ischemic stroke, hemorrhage, arteriosclerosis, atherosclerosis, restenosis, diabetic arteriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrhythmias, ventricular fibrillation, His bundle arrhythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aortic and peripheral aneurysms, aortic dissection, inflammation of the aorta, occlusion of the abdominal aorta and its branches, peripheral vascular disorders, occlusive arterial disorders, peripheral atherosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphedema, lipedema, unstable angina, reperfusion injury, post pump syndrome, ischemia-reperfusion injury, and the like.

b. Immune- or Inflammation Related Disease Tissue

One of ordinary skill in the art will appreciate that a wide variety of disease tissues from a subject can be used to prepare disease cells, disease cell aggregates and/or disease tissue fragments according to a subject method. A preferred disease tissue is an immune or inflammation related disease tissue. A suitable immune or inflammation related disease tissue includes, but is not limited to, a tissue obtained from a subject having at least one of, or at least one inflammation related to, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, Crohn's disease, systemic lupus erythematosis, antiphospholipid syndrome, iridocyclitis, uveitis, optic neuritis, idiopathic pulmonary fibrosis, systemic vasculitis, Wegener's granulomatosis, sarcoidosis, orchitis, vasectomy or vasectomy reversal procedures, allergic atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma, hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, type I or type II diabetes, nephrosis, atopic diseases, hypersensitivity reactions, allergic rhinitis, hay fever, perennial rhinitis, conjunctivitis, endometriosis, asthma, urticaria, systemic anaphylaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, receptor hypersensitivity reactions, chronic obstructive pulmonary disease (COPD), Graves disease, Raynoud's disease, type B insulin-resistant diabetes, asthma, myasthenia gravis, antibody-meditated cytotoxicity, gene therapy inflammation (e.g., adenovirus, AAV, vaccinia, DNA or RNA, Moloney murine leukemia virus (MMLV) and the like), type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic, idiopathic, Wilson's disease, hemachromatosis, alpha-1-antitrypsin deficiency, diabetic retinopathy, Hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, cd3 therapy, cytokine therapy, chemotherapy, radiation therapy (e.g., including but not limited to asthenia, anemia, cachexia, and the like), chronic salicylate intoxication, and the like (See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000)).

c. Infectious Disease Tissue

One of ordinary skill in the art will appreciate that a wide variety of disease tissues from a subject can be used to prepare disease cells, disease cell aggregates and/or disease tissue fragments according to a subject method. A preferred disease tissue is an infectious disease tissue. A suitable infectious disease tissue includes, but is not limited to, a tissue obtained from a subject having at least one of: acute or chronic bacterial infection, acute and chronic parasitic or infectious processes, including bacterial, viral and fungal infections, HIV infection, HIV neuropathy, meningitis, hepatitis (A, B or C, or the like), septic arthritis, peritonitis, pneumonia, epiglottitis, *e. coli* 0157:h7, hemolytic uremic syndrome, thrombolytic thrombocytopenic purpura, malaria, dengue hemorrhagic fever, leishmaniasis, leprosy, toxic shock syndrome, streptococcal myositis, gas gangrene, *mycobacterium tuberculosis*, *mycobacterium avium* intracellulare, *pneumocystis carinii* pneumonia, pelvic inflammatory disease, orchitis, epidydimitis, legionella, Lyme disease, influenza A, Epstein- Barr virus, vital-associated hemaphagocytic syndrome, viral encephalitis, aseptic meningitis, and the like.

d. Neurologic Disease Tissue

One of ordinary skill in the art will appreciate that a wide variety of disease tissues from a subject can be used to prepare disease cells, disease cell aggregates and/or disease tissue fragments according to a subject method. A preferred disease tissue is a neurologic disease tissue. A suitable neurologic disease tissue includes, but is not limited to, a tissue obtained from a subject having at least one of: neurodegenerative disease; multiple sclerosis; migraine; headache; AIDS dementia complex; demyelinating disease, such as multiple sclerosis and acute transverse myelitis; extrapyramidal and cerebellar disorder, such as lesions of the corticospinal system; disorder of the basal ganglia or cerebellar disorder; hyperkinetic movement disorder, such as Huntington's Chorea and senile chorea; drug-induced movement disorders, such as those induced by drugs which block CNS dopamine receptors; hypokinetic movement disorder, such as Parkinson's disease; Progressive supranucleo Palsy; structural lesions of the cerebellum; spinocerebellar degeneration, such as spinal ataxia, Friedreich's ataxia, cerebellar cortical degeneration, multiple systems degeneration (Mencel, Dejerine-Thomas, Shi-Drager, and Machado-Joseph); systemic disorder (Refsum's disease, abetalipoprotemia, ataxia, telangiectasia, and mitochondrial multisystem disorder); demyelinating core disorder, such as multiple sclerosis, acute transverse myelitis; disorder of the motor unit, such as neurogenic muscular atrophies (anterior hom cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis; Hallerrorden-Spatz disease; and Dementia pugilistica, and the like.

2. Obtaining and Providing a Tissue Sample

In some embodiments of the present invention, the method of processing a tissue sample to prepare a plurality of cells, a plurality of cell aggregates and/or tissue fragments comprises the step of obtaining a tissue sample from a tissue from which the cells, cell aggregates and/or tissue fragments can be prepared. In some embodiments of the present invention, a tissue sample is a tissue biopsy.

i. Needle Biopsy

In some embodiments of the present invention, a tissue biopsy is a needle biopsy. In some embodiments of the present invention, a tissue biopsy is a core needle biopsy. In some embodiments of the present invention, a tissue biopsy is a fine needle biopsy.

ii. Surgical Biopsy

In some embodiments of the present invention, a tissue biopsy is a surgical biopsy.

3. Providing a Device

In some embodiments of the present invention, the method of processing a tissue sample to prepare a plurality of cells, a plurality of cell aggregates and/or tissue fragments comprises the step of providing a device for placing in a tissue sample. Useful devices for preparing cells and cell aggregates are described herein. In some embodiments, a two-stage filter device is provided. In some embodiments, a two-membrane device is provided.

For practicing a method of processing a tissue sample to prepare a plurality of cells, a plurality of cell aggregates and/or tissue fragments, a cell culture medium may be filled into the device provided. As one of ordinary skill in the art appreciates, the type of cell culture medium added may depend on the type of tissue from which single cells and cell aggregates will be prepared. Many nutrient media supporting the culturing and growth of cells for use in the present application are known in the art and are commercially available. Such medium includes, but is not limited to RPMI-1640, DMEM, Ham's F-10, F-12, McCoy's fA modified Medium and Ames Media. Also known in the art are various medium supplements, including, but not limited to animal-derived serum, growth factors, vitamins, nutrients and hormones. Growth factor addition may be specific for a specific tissue or cell type. In some embodiments, the cell culture medium does not include serum, i.e., a serum-free culture medium will be used.

All medium components may be added at the start of the processing step (see herein) or added continuously or batchwise, as desired, during the processing step. In some embodiments of the present invention, a cell culture medium is continuously flown through a device for preparing cells and cell aggregates. This is schematically shown in FIGS. 1 and 3.

Standard cell culture techniques well known in the art can be applied. Medium components preferably are sterilized either together or separately prior to use.

4. Placing a Tissue Sample into a Device

In some embodiments of the present invention, the method of processing a tissue sample to prepare a plurality of cells, a plurality of cell aggregates and/or tissue fragments comprises the step of placing a tissue sample into a device of the present invention, e.g., into a two-stage filter device or a two-membrane device. This step can be done manually. Alternatively, if a large number of tissues is being processed, this step can be automatized.

5. Processing a Tissue Sample and Preparing a Plurality of Cells Cell Aggregates and/or Tissue Fragments In some embodiments of the present invention, the method of processing a tissue sample to prepare a plurality of cells, a plurality of cell aggregates and/or tissue fragments comprises the step of processing a tissue sample from which cells, cell aggregates and/or tissue fragments can be prepared. Upon processing the tissue sample, a mixture is generated comprising a plurality of cells, a plurality of cell aggregates and/or tissue fragments.

Method described herein are useful for preparing cell aggregates from any tissue sample described herein.

Cell aggregates and tissue fragments prepared by a subject method herein, comprise a plurality of cells, more specifically, a plurality of cancer cells, or a plurality of disease cells. In some embodiments, a cell aggregate or tissue fragment comprises a plurality of living cells.

In some embodiments, the cell aggregates and tissue fragments prepared according to a subject method are substantially uniform in size. In some embodiments, the cell aggregates and tissue fragments prepared according to a subject method are substantially uniform in numbers of cells.

The exact number of cells per cell aggregate or tissue fragment or the actual size of the cell aggregate or tissue fragment, however, are not critical. As one of ordinary skill in the art will appreciate, and as described herein, the duration of the processing operation, the type of device used and the type of tissue sample processed primarily determine the size of a cell aggregate or tissue fragment and the number of cells in a cell aggregate or tissue fragment. zzzz A cell aggregate prepared according to a subject method may include a minimal number of cells (e.g., two, three, four, five, six, seven, eight, nine or ten cells) per cell aggregate. Some of the very small cell aggregates, such as aggregates having about 2 to 5 cells may not be efficiently separated from the plurality of single cells. However, as described herein the devices can be configured to predominantly prepare cell aggregates having more than about 5 cells. In some embodiments, a cell aggregate comprises between about 10 and about 100 cells. In some embodiments, a cell aggregate comprises between about 100 and about 200 cells. In some embodiments, a cell aggregate comprises between about 200 and about 300 cells. In some embodiments, a cell aggregate comprises between about 300 and about 400 cells. In some embodiments, a cell aggregate comprises between about 400 and about 500 cells. In some embodiments, a cell aggregate comprises between about 500 and about 600 cells. In some embodiments, a cell aggregate comprises between about 600 and about 700 cells. In some embodiments, a cell aggregate comprises between about 700 and about 800 cells. In some embodiments, a cell aggregate comprises between about 800 and about 900 cells. In some embodiments, a cell aggregate comprises between about 900 and about 1,000 cells. In some embodiments, a cell aggregate comprises between about 1,000 and about 2,000 cells. In some embodiments, a cell aggregate comprises between about 2,000 and about 2,000 cells. In some embodiments, a cell aggregate comprises between about 2,000 and about 3,000 cells. In some embodiments, a cell aggregate comprises between about 3,000 and about 5,000 cells. In some embodiments, a cell aggregate comprises between about 5,000 and about 10,000 cells. In some embodiments, a cell aggregate comprises fewer than about 10,000 cells. A cell conglomerate comprising more than 10,000 cells is referred herein as a tissue fragment.

A cell aggregate prepared according to a subject method can comprise any size. In some embodiments, a cell aggregate is from about 50 µm to about 100 µm. In some embodiments, a cell aggregate is from about 100 µm to about 200 µm. In some embodiments, a cell aggregate is from about 200 µm to about 300 µm. In some embodiments, a cell aggregate is from about 300 µm to about 400 µm. In some embodiments, a cell aggregate is from about 400 µm to about 500 µm. In some embodiments, a cell aggregate is from about 500 µm to about 600 µm. In some embodiments, a cell aggregate is from about 600 µm to about 1,000 µm.

In some embodiments, wherein a two-stage filter device or a two-membrane device is used for preparing a plurality of cells, a plurality of cell aggregates and/or tissue fragments, the size of the pores of the first plurality of pores substantially determines the size of a cell aggregate or tissue fragment that can be collected practicing methods of the present invention. If a cell aggregate or tissue fragment is larger in size than the sizes of pores within the first plurality of pores in a device described herein, then the cell aggregate or tissue fragment cannot pass through the first plurality of pores and thus, cannot be collected from the second container or from a collection channel attached thereto. Instead those cell aggregates and tissue fragments may be collected from within the first container. If a cell aggregate is smaller in size than the sizes of pores within the first and second plurality of pores in a device described herein, then the cell aggregate pass through the first and second plurality of pores and thus, also cannot be collected in the second container or through a collection channel attached thereto. Those cell aggregates may be collected from the third container or a collection channel attached thereto. If a cell aggregate is smaller in size than the sizes of pores within the first plurality of pores in a device described herein and larger than the sizes of pores within the second plurality of pores in a device described herein, the cell aggregate can pass through the first plurality of pores, but not through the second plurality of pores and thus, can be collected from the second container or a collection channel attached thereto (FIG. 4).

Depending on the size of a cell aggregate or tissue fragment to be prepared, one of skill in the art will readily appreciate to choose appropriate containers having the most suitable sized pores. For example, assuming a mammalian cell has an average diameter of about 20 µm and it is desired to prepare a cell aggregate of about 1,000 cells, one of ordinary skill in the art (assuming the 1,000 cells are tightly packed in a cube-like shape) practicing a method using, e.g., a two-stage filter devices as described herein could select a first container wherein the pores of the first plurality of pores are about 250 µm in diameter and a second container wherein the size of pores of the second plurality of pores would be about 30 µm in diameter. Making such selection that person would be able to collect the desired size cell aggregate (see FIG. 4). As one of ordinary skill in the art will appreciate, other suitable pore sizes can be chosen.

In some embodiments, the cell aggregates prepared according to a subject method are substantially uniform in shape. Cell aggregates can be of various shapes, such as, for example, sphere-like, cylinder-like (substantially the same height and diameter); rod-like, cube-like, and the like.

As described herein, many tissue samples are suitable to prepare a plurality of cells, a plurality of cell aggregates and/or tissue fragments according to a subject method. Thus, many cell types can form a plurality of cells, a plurality of cell aggregates and/or tissue fragments.

Subject methods described herein are suitable for preparing tissue fragments, cell aggregates and single cells. As one of ordinary skill in the art will appreciate the ratio of single cells vs. cell aggregates vs. tissue fragments prepared from a tissue sample depends, among others, on the type of tissue sample, the choice of device provided herein, the extent of processing and the presence of components in the cell culture medium (see herein).

Without being bound by theory, it is believed that the tissue fragments and cell aggregates, in particular disease tissue fragments and disease cell aggregates, prepared by a subject method display growth kinetics, metabolic traits and responses to an extracellular matrix that substantially mimics that of an in vivo tissue, particularly that of an in vivo disease tissue, such as an in vivo cancer tissue and others described herein.

6. Activating a Device

In some embodiments of the present invention, the method of processing a tissue sample to prepare a plurality of cells, a plurality of cell aggregates and/or tissue fragments comprises the step of activating a device into which a tissue sample has been placed. Activation of a device depends on the choice of device. For example activating a two-stage filter device or a two-membrane device on which a rotating blade is being activated, requires the device being switched on.

7. Adding an Enzyme to a Mixture Comprising Cell Culture Medium and a Tissue Sample In some embodiments of the present invention, the method of processing a tissue sample to prepare a plurality of cells, a plurality of cell aggregates and/or tissue fragments comprises the step of adding an enzyme to a mixture comprising cell culture medium and a tissue sample. This is particularly useful if it is desired to process the tissue sample not only mechanically using a device described herein, but, in addition, also enzymatically.

In some embodiments, the enzyme is selected from the group consisting of a DNAse, a lipase, a proteinase, collagenase, and trypsin.

In some embodiments, a cell culture medium for use in a subject method comprises one or more of the following polypeptides: a proteinase, a collagenase, a DNAse, a lipase, and trypsin.

8. Obtaining a Sample of the Processing Mixture

In some embodiments of the present invention, the method of processing a tissue sample to prepare a plurality of cells, a plurality of cell aggregates and/or tissue fragments comprises the step of obtaining a sample of the processing mixture. Such sample might be taken for assessing the processing of the tissue and can be taken conveniently using a pipette or similar device.

A sample collected from a third container of a device described herein may comprise primarily single cells and small cell aggregates (depending on the size of pores used in the first and second walls).

A sample collected from a second container of a device described herein may comprise primarily cell aggregates (depending on the size of pores used in the first and second walls).

A sample collected from a first container of a device described herein may comprise primarily tissue fragments (depending on the size of pores used in the first wall).

9. Analyzing a Sample of the Processing Mixture for the Presence of Single Cells, Cell Aggregates and/or Tissue Fragments In some embodiments of the present invention, the method of processing a tissue sample to prepare a plurality of cells, a plurality of cell aggregates and/or tissue fragments comprises the step of analyzing a sample of the processing mixture for the presence of single cells, cell aggregates and/or tissue fragments. Such analysis can be performed on a test sample by, e.g., using a light microscope.

10. Analyzing a Sample of the Processing Mixture for Quantifying Single Cells, Cell Aggregates and/or Tissue fragments In some embodiments of the present invention, the method of processing a tissue sample to prepare a plurality of cells, a plurality of cell aggregates and/or tissue fragments comprises the step of analyzing a sample of the processing mixture for quantifying the number or amount of single cells, cell aggregates and/or tissue fragments. Such analysis can be done on a test sample by, e.g., using a light microscope.

11. Separating a Plurality of Cell Aggregates from a Plurality of Single Cells and/or Tissue Fragments In some embodiments of the present invention, the method of processing a tissue sample to prepare a plurality of cells, a plurality of cell aggregates and/or tissue fragments comprises the step of separating a cell aggregate from a plurality of single cells or the step of separating a cell aggregate from a tissue fragment or the step of separating a tissue fragment from a plurality of single cells. As described herein, using filters or membranes having different pore sizes allow the efficient separation of larger size cell aggregates or tissue fragments from the smaller size single cells. Smaller size single cells pass through smaller pores through which larger cell aggregates and tissue fragments don't pass.

12. Collecting a Cell Aggregate

In some embodiments of the present invention, the method of processing a tissue sample to prepare a plurality of cells, a plurality of cell aggregates and/or tissue fragments comprises the step of collecting a cell aggregate. Using, e.g., a two-stage filter device, cell aggregates may be collected from a collection channel if present (see FIG. 4).

13. Separating a Plurality of Single Cells

Figure 6:
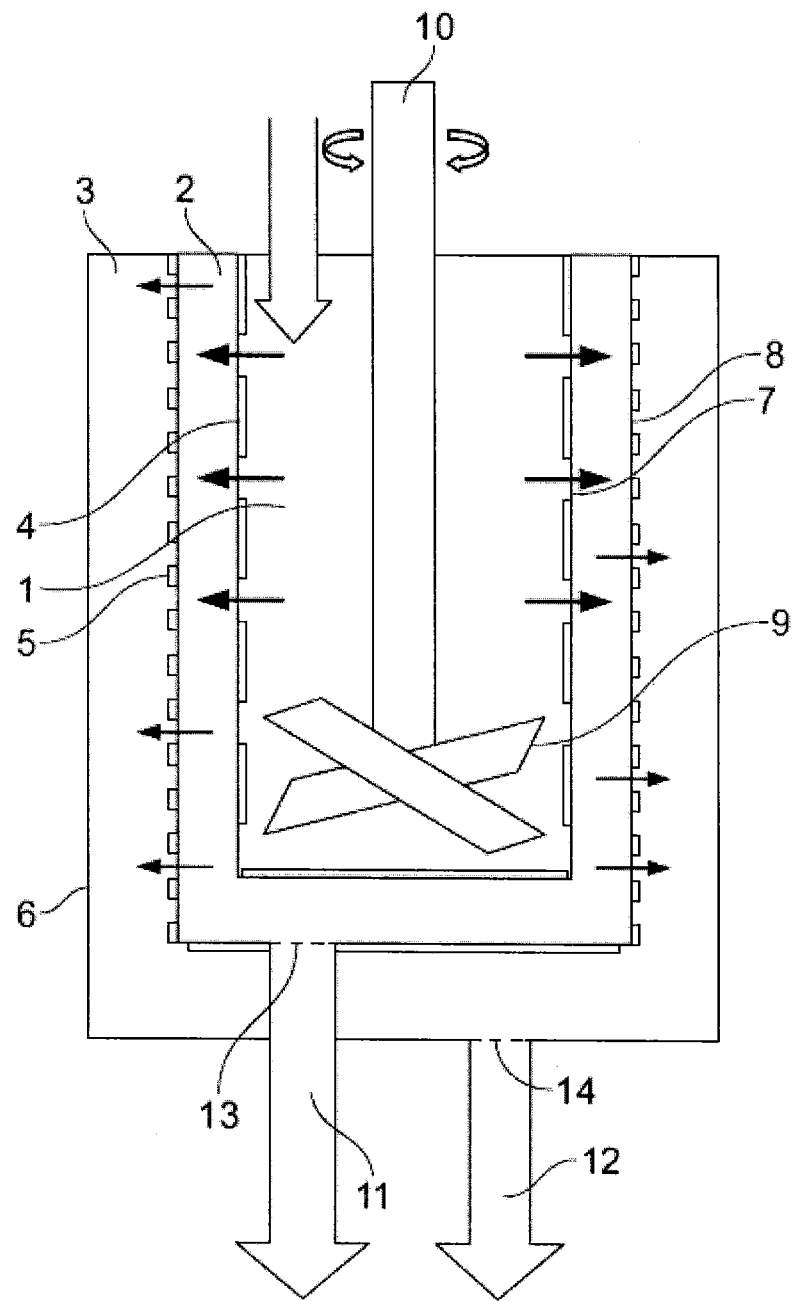
Figure 7:
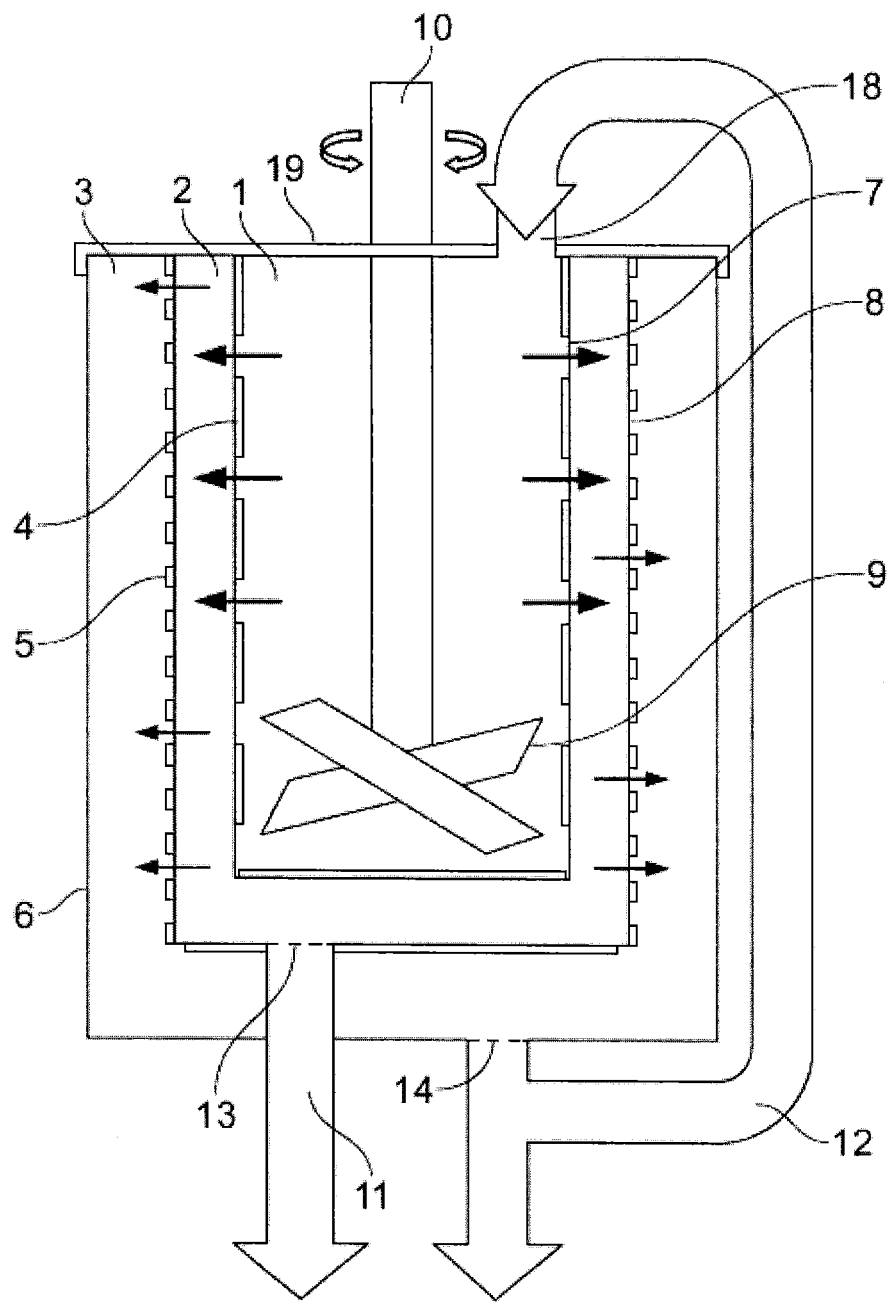
FIG. 7 schematically depicts an embodiment of a device of the present invention for the processing of a tissue sample to prepare a plurality of cells, a plurality of cell aggregates and tissue fragments. This device embodiment is similar to the device depicted in FIG. 1, however, in this embodiment, after passing through gate 14, channel 12 allows for both redirecting fluid (e.g., cell culture medium) back into first container 1 and collecting fluid and single cells. In this embodiment, fluid or medium enters the first container 1 through an inlet 18. Optionally, the device may have a lid 19. Individual parts are as described in FIG. 1 and herein.
Figure 8:
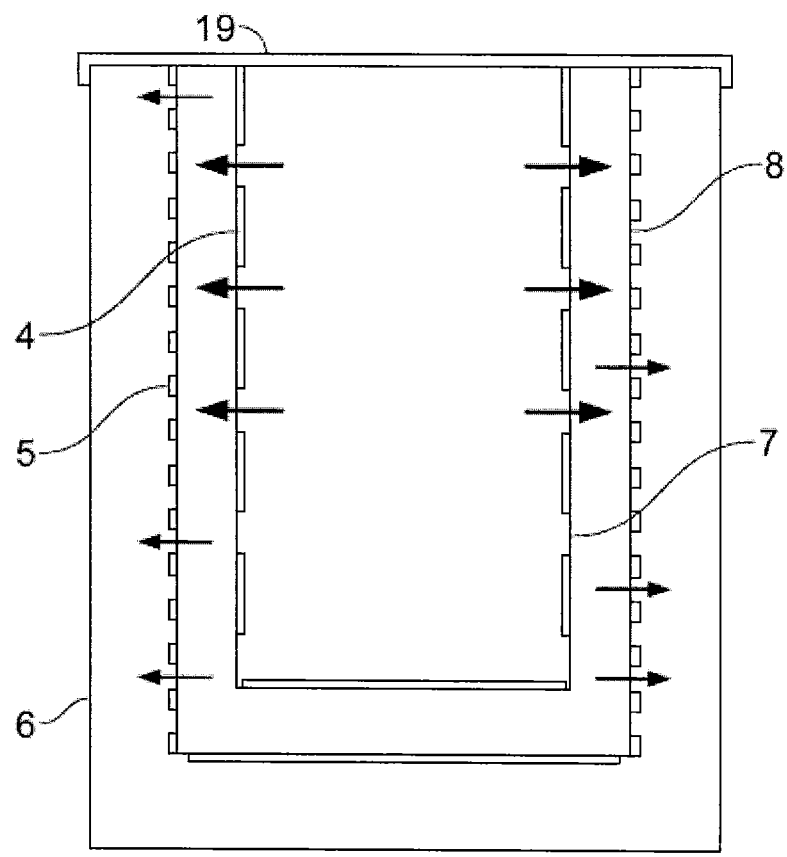
FIG. 8 schematically depicts a two-membrane device inserted into a container. The container is shown in light grey. Optionally, the device may have a lid 19. Individual parts are as described in FIG. 1 and herein.

In some embodiments of the present invention, the method of preparing cells comprises the step of collecting a plurality of cells. Using a two-stage filter device, a plurality of cells, e.g., can be collected through channel 12 (FIGS. 6, 7).

14. Separating a Tissue Fragment

In some embodiments of the present invention, the method of preparing cells comprises the step of collecting a tissue fragment. Using a two-stage filter device, a tissue fragment, e.g., can be collected from the bottom of a first container.

15. Testing and/or Confirming Cell Identity

In some embodiments of the present invention, the method of preparing cells comprises the step of testing and/or confirming the identity of a cell, e.g., whether a a plurality of cells, a plurality of cell aggregates and/or tissue fragments prepared according to a subject method comprise desired cells, such as a disease cell. Using microscopy methods, immunohistological methods and cell-specific antibodies known in the art, the identity of prepared cells, cell aggregates and/or tissue fragments can be tested and/or confirmed.

B. Methods of Using Cells, Cell Aggregates and/or Tissue Fragments

The present invention provides various methods of using a cell, a plurality of cells a cell aggregate, a plurality of cell aggregates, a tissue fragment or a plurality of tissue fragments prepared by a subject method above.

In some embodiments of the present invention, a cell, a cell aggregate and/or a tissue fragment is used for culturing the cell, cell aggregate and/or tissue fragment.

In some embodiments of the present invention, a cell, a cell aggregate and/or a tissue fragment t is grown in suspension.

In some embodiments of the present invention, a cell, a cell aggregate and/or a tissue fragment is grown in a cell culture plate.

In some embodiments of the present invention, a cell, a cell aggregate and/or a tissue fragment is used for a cell proliferation assay.

In some embodiments of the present invention, a cell, a cell aggregate and/or a tissue fragment is used for a cell death assay.

In some embodiments of the present invention, a cell, a cell aggregate and/or a tissue fragment is used for an angiogenesis assay.

In some embodiments of the present invention, a cell, a cell aggregate and/or a tissue fragment is used for a metastasis assay.

In some embodiments of the present invention, a cell, a cell aggregate and/or a tissue fragment is used for identification and distinguishing between cancer and normal cells.

In some embodiments of the present invention, a cell, a cell aggregate and/or a tissue fragment is used for quantifying proliferation of cancer and normal cells.

In some embodiments of the present invention, a cell, a cell aggregate and/or a tissue fragment is frozen.

In some embodiments of the present invention, a cell, a cell aggregate and/or a tissue fragment is transported to a laboratory for further analysis.

In some embodiments of the present invention, a plurality of single cells is used for coaxing the plurality of single cells to form a cell aggregate in vitro. Thus, many cell types can form a cell aggregate.

In some embodiments of the present invention, a cell, a cell aggregate and/or a tissue fragment is used to study tumor formation and tumor growth.

In some embodiments of the present invention, a cell, a cell aggregate and/or a tissue fragment is used to evaluate the effectiveness of a known drug. In some embodiments of the present invention, a cancer cell, cancer cell aggregate and/or cancer tissue fragment is used to evaluate the effectiveness an anti-cancer drug.

In some embodiments of the present invention, a cancer cell, a cancer cell aggregate and/or a cancer tissue fragment is used to identify a molecular mechanism of cancer.

In some embodiments of the present invention, a cell, a cell aggregate and/or a tissue fragment is used to observe an effect of a known drug. In some embodiments of the present invention, a cancer cell, a cancer cell aggregate and/or a cancer tissue fragment is used to observe an effect of an anti-cancer drug.

In some embodiments of the present invention, a cancer cell, a cancer cell aggregate and/or a cancer tissue fragment is used to identify an agent which modulates (inhibits, promotes, or delays) cancer progression or which modulates (delays, increases or decreases) tumor sensitivity to radiation therapy and/or chemotherapy.

V. Kits

For use in diagnostic, research, and therapeutic applications suggested above, kits are also provided by the invention. In the diagnostic and research applications such kits may include any or all of the following: assay reagents, buffers, a device of the present invention, a two-stage filter device, a two-membrane device, and the like. A therapeutic product may include sterile saline or another pharmaceutically acceptable emulsion and suspension base.

In some embodiment of the present invention, a kit comprises a two-stage filter device. Optionally, the kit includes one or more components, such as a tissue, a washing solution, a disaggregation medium, a shipping medium, and/or an instruction manual as described herein. Typically, these components, other than an instruction manual, are provided in a container.

In some embodiments, the present invention provides kits for practicing methods of the present invention, including, but not limited to, processing a tissue sample to prepare a plurality of cells, a plurality of cell aggregates and/or tissue fragments. In some embodiments of the present invention, a kit comprises (i) a device as described herein, and (ii) an instruction manual describing the use of (i) for practicing methods of the present invention, including, but not limited to, processing a tissue sample to prepare a plurality of cells, a plurality of cell aggregates and/or tissue fragments.

In some embodiments of the present invention, a kit comprises (i) a two-stage filter device as described herein, and (ii) an instruction manual describing the use of (i) for practicing methods of the present invention, including, but not limited to, processing a tissue sample to prepare a plurality of cells, a plurality of cell aggregates and/or tissue fragments.

In some embodiments of the present invention, a kit comprises (i) a two-membrane device as described herein, and (ii) an instruction manual describing the use of (i) for practicing methods of the present invention, including, but not limited to, processing a tissue sample to prepare a plurality of cells, a plurality of cell aggregates and/or tissue fragments.

An instructional material may contain directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

A wide variety of kits and components can be prepared according to the present invention, depending upon the intended user of the kit and the particular needs of the user.

Additional kit embodiments of the present invention include optional functional components that would allow one of ordinary skill in the art to perform any of the method variations described herein.

Preferred embodiments of this invention are described herein, including the best mode known to the inventors for carrying out the invention. Of course, variations, changes, modifications and substitution of equivalents on those preferred embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

VI. Examples

The below examples are meant to illustrate specific embodiments of the methods and compositions described herein and should not be construed as limiting the scope of the invention in any way.

Example 1

General Methods

The practice of the present invention will employ, unless otherwise indicated herein, conventional techniques of cell biology, molecular biology, microbiology, virology, recombinant DNA, and so forth which are within the skill of the art.

Such techniques are explained fully in the literature. See e.g., Sambrook, Fritsch, and Maniatis, *Molecular Cloning: A Laboratory Manual*, Second Edition (1989), *Oligonucleotide Synthesis* (M. J. Gait Ed., 1984), *Animal Cell Culture* (R. I. Freshney, Ed., 1987), the series *Methods In Enzymology* (Academic Press, Inc.); *Gene Transfer Vectors For Mammalian Cells* (J. M. Miller and M. P. Calos eds. 1987), *Current Protocols Ii Molecular Biology* (F. M. Ausubel, R. Brent, R. E. Kingston, D. D. Moore, J. G. Siedman, J. A. Smith, and K. Struhl, eds., 1987).

What is claimed is:

1. A device for processing a tissue sample to prepare a cell aggregate or tissue fragment, the device comprising:
    (i) a first container comprising a first wall;
    (ii) a plurality of cutting blades having a sharp edge pointing inwards into the first container;
    (iii) a first plurality of pores located in the first wall of the first container; and
    (iv) a second container comprising a second wall;
    wherein the plurality of blades, upon contacting the tissue sample, is capable of processing the tissue sample to prepare a cell aggregate or tissue fragment;
    wherein the first plurality of pores comprises pore members having a size permitting a single cell and a cell aggregate to pass through, but not permitting the tissue sample to pass through;
    wherein the second wall comprises a second plurality of pores;
    wherein the first container is nested within the second container; and
    wherein rotational force is used to transport the single cell and the cell aggregate through the first plurality of pores.

2. The device according to claim 1, wherein the size of the pores of the first plurality of pores is selected to permit passing through of a single cell and a cell aggregate comprising more than 10 cells but essentially do not permit passing through of a majority of tissue fragments comprising more than about 10,000 cells.

3. The device according to claim 1, wherein the pores of the first plurality of pores have a diameter selected from the group of ranges consisting of from about 50 μm to about 100 μm, from about 100 μm to about 200 μm, from about 200 μm to about 300 μm, from about 300 μm to about 400 μm, from about 400 μm to about 500 μm, from about 500 μm to about 600 μm and from about 600 μm to about 1,000 μm.

4. The device according to claim 1, wherein the shape of the first container is selected from the group consisting of cylindrical, oval, rectangular, square, and hexagonal.

5. The device according to claim 1, wherein the plurality of cutting blades is attached to a shaft.

6. The device according to claim 5, wherein upon activation of the device, the shaft and the plurality of cutting blades rotate inside the first container.

7. The device according to claim 6, wherein the plurality of cutting blades rotate at a speed selected from the group of ranges consisting of from about 50 rpm to about 200 rpm, from about 100 rpm to about 500 rpm, from about 200 rpm to about 1,000 rpm, from about 500 rpm to about 2,000 rpm, from about 2,000 rpm to about 3,000 rpm, from about 3,000 rpm to about 5,000 rpm, and from about 5,000 rpm to about 10,000 rpm.

8. The device according to claim 1, further comprising:
    (v) an inlet for introducing a cell culture medium.

9. The device according to claim 1, further comprising:
    (v) a lid covering an upper opening of the first and second containers.

10. The device according to claim 1, wherein the size of the second plurality of pores is different than the size of the pores of the first plurality of pores.

11. The device according to claim 1, wherein the pores of the first plurality of pores are larger in diameter than the pores of the second plurality of pores.

12. The device according to claim 1, wherein the size of the pores of the second plurality of pores is selected to permit passing through of a single cell but essentially do not permit passing through of a majority of a cell aggregate comprising more than 10 cells.

13. The device according to claim 1, wherein the pores of the second plurality of pores have a diameter ranging from about 10 μm to about 50 μm.

14. The device according to claim 1, wherein the shape of the second container is selected from the group consisting of cylindrical, oval, rectangular, square, and hexagonal.

15. The device according to claim 1, wherein the second container comprises a collection channel permitting the collection of the cell aggregate.

16. The device according to claim 15, wherein the second container further comprises a gate at the collection channel.

17. The device according to claim 1, further comprising:
    (v) a third container comprising a third wall;
    wherein the second container is nested within the third container.

18. The device according to claim 17, wherein the shape of the third container is selected from the group consisting of cylindrical, oval, rectangular, square, and hexagonal.

19. The device according to claim 17, wherein the third container comprises a channel permitting transporting a cell culture medium from the third container into the first container.

20. The device according to claim 17, wherein the third container comprises a channel permitting collection of cells.

21. A method of processing a tissue sample to prepare a cell aggregate and/or a tissue fragment using a device of claim 1, the method comprising the steps of:
    (a) placing a tissue sample into the device of claim 1;
    (b) contacting the tissue sample to the plurality of blades;
    (c) applying a rotational force; and
    (d) permitting passing of cell aggregates through the first plurality of pores;
    whereby the tissue is processed to generate the cell aggregate and/or the tissue fragment.

22. The method according to claim 21, wherein the tissue sample is obtained by a needle biopsy obtained from a subject.

23. The method according to claim 21, wherein the tissue sample is obtained by a surgical biopsy obtained from a subject.

24. The method according to claim 21, wherein the tissue sample is a cancerous tissue sample.

25. The method according to claim 24, wherein the cancerous tissue sample is selected from the group consisting of a lung cancer tissue, a sarcoma tissue, a gastrointestinal cancer tissue, a genitourinary tract cancer tissue, a liver cancer tissue, a skin cancer tissue, a gynecological cancer tissue, a bone cancer tissue, a nervous system cancer tissue, a hematologic cancer tissue, and an adrenal gland cancer tissue.

26. The method according to claim 24, wherein the cancerous tissue sample comprises a cancer stem cell.

27. The method according to claim 21, wherein the tissue sample is a disease tissue sample.

28. The method according to claim 27, wherein the disease tissue sample is selected from the group consisting of a cardiovascular disease tissue, an immune- or inflammation related disease tissue, an infectious disease tissue, and a neurologic disease tissue.

29. The method according to claim 21, wherein the cell aggregate is selected from the group consisting of a cell aggregate comprising from about 10 to about 500 cells, a cell aggregate comprising from about 20 to about 200 cells, and a cell aggregate comprising from about 50 to about 100 cells.

30. The method according to claim 21, wherein the rotational force is selected from the group of ranges consisting of from about 50 rpm to about 200 rpm, from about 100 rpm to about 500 rpm, from about 200 rpm to about 1,000 rpm, from about 500 rpm to about 2,000 rpm, from about 2,000 rpm to about 3,000 rpm, from about 3,000 rpm to about 5,000 rpm, and from about 5,000 rpm to about 10,000 rpm.

* * * * *